(12) United States Patent
Cerri et al.

(10) Patent No.: US 8,022,203 B2
(45) Date of Patent: Sep. 20, 2011

(54) AMINO DERIVATIVES OF BETA-HOMOANDROSTANES AND BETA-HETEROANDROSTANES

(75) Inventors: Alberto Cerri, Milan (IT); Barbara Moro, Vittore Olona (IT); Maco Torri, Rho (IT); Giulio Carzana, Milan (IT); Giuseppe Bianchi, Milan (IT); Mara Ferrandi, Milan (IT); Patrizia Ferrari, Varese (IT); Maria Pia Zappavigna, Magenta (IT); Leonardo Banfi, Novate Milanese (IT); Giuseppe Giacalone, Novara (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 347 days.

(21) Appl. No.: 12/305,571

(22) PCT Filed: May 31, 2007

(86) PCT No.: PCT/EP2007/055366
§ 371 (c)(1),
(2), (4) Date: Mar. 16, 2009

(87) PCT Pub. No.: WO2007/147713
PCT Pub. Date: Dec. 27, 2007

(65) Prior Publication Data
US 2009/0209506 A1    Aug. 20, 2009

(30) Foreign Application Priority Data

Jun. 23, 2006 (EP) .................................... 06116001

(51) Int. Cl.
| | |
|---|---|
| *C07D 223/14* | (2006.01) |
| *C07D 281/08* | (2006.01) |
| *C07D 411/00* | (2006.01) |
| *C07D 207/00* | (2006.01) |
| *A61K 31/58* | (2006.01) |
| *A61K 31/55* | (2006.01) |
| *A61K 31/44* | (2006.01) |

(52) U.S. Cl. ........ 540/519; 540/576; 540/546; 548/525; 548/566; 514/172; 514/176; 514/212.04; 514/284

(58) Field of Classification Search ....................... None
See application file for complete search history.

(56) References Cited

U.S. PATENT DOCUMENTS

| | | | | |
|---|---|---|---|---|
| 2,806,029 | A | * 9/1957 | Mazur | ........................ 540/519 |
| 3,136,584 | A | * 6/1964 | Whitlock | .................... 406/129 |
| 3,328,408 | A | 6/1967 | Gordon et al. | |
| 5,914,324 | A | 6/1999 | De Munari et al. | |
| 6,825,208 | B2 | * 11/2004 | Zhou et al. | .................... 514/284 |
| 7,727,976 | B2 | * 6/2010 | Bhat et al. | ..................... 514/176 |

OTHER PUBLICATIONS

De Munari, et al., Structure-Based Design and Synthesis of Novel. Potent Na+,K+-ATPase Inhibitors Derived from a 5a,14a-Androstane Scaffold as Positive Inotropic Compounds, Journal of Medicinal Chemistry, 2003, 46(17):3644-3654.

Razdan, et al., Drugs Derived from Cannabinoids. 6. Synthesis of Cyclic Analogues of Dimethylheptylpyran, Journal of Medicinal Chemistry, 1976, 19(5):719-721.

Starka, et al., The Effect of Phytogenic Brassinosteroid Steroidal Hormones on Transport of 86Rb+ Ions intoHuman Erythrocytes, Database CA, 1997, 98(1):21-25.

* cited by examiner

*Primary Examiner* — Kamal Saeed
*Assistant Examiner* — Nyeemah A Grazier
(74) *Attorney, Agent, or Firm* — Lucas & Mercanti LLP

(57) ABSTRACT

New aminoalkoxyimino derivatives at position 3 of substituted B-homoandrostanes and B-heteroandrostanes, processes for their preparation, and to pharmaceutical compositions containing them for the treatment of cardiovascular disorders, such as heart failure and hypertension. In particular compounds having the general formula (I) are described, where the radicals have the meanings described in detail in the application.

12 Claims, No Drawings

AMINO DERIVATIVES OF BETA-HOMOANDROSTANES AND BETA-HETEROANDROSTANES

FIELD OF THE INVENTION

The present invention relates to new aminoalkoxyimino derivatives at position 3 of substituted B-homoandrostanes and B-heteroandrostanes, processes for their preparation, and to pharmaceutical compositions containing them for the treatment of cardiovascular disorders, such as heart failure and hypertension.

BACKGROUND OF THE INVENTION

Cardiovascular diseases are still the first cause of morbidity and mortality in the western world; among these, hypertension and heart failure are two of the most frequent diseases. Hypertension is one of the most important cardiovascular risk factors and more than one third of population over 60 suffer from this disease. Congestive heart failure affects 1-2% of the population and even 10% of the very elderly; the percentage is expected to rise (Sharpe N., et al, *The Lancet*, 1998, 352, (suppl. 1), 3-17). Beside, hypertension may be one of the most important causes of heart failure in the elderly (*Eur. Heart J.*, 2001, 22, 1527-1560). Although a number of effective drugs are available for the treatment of both hypertension and heart failure, further research is in progress to find more effective and safe compounds. Several drugs are used in combination for the treatment of heart failure, and among positive inotropic agents, digoxin is the most prescribed digitalis cardiac glycoside that can improve the myocardial performance. A very well-known drawback of digitalis drugs is their arrhythmogenic side-effect. Evidence of digitalis toxicity emerges at two- to three-fold higher serum concentration than the therapeutic dose, such as disturbances of conduction and cardiac arrhythmias which are characteristics of digitalis toxicity (Hoffman, B. F.; Bigger, J. T, *Digitalis and Allied Cardiac Glycosides. In The Pharmacological Basis of Therapeutics*, 8$^{th}$ ed.; Goodman Gilman, A.; Nies, A. S.; Rail, T. W.; Taylor, P., Eds.; Pergamon Press, New York, 1990, pp 814-839).

The capability of the natural digitalis compounds to increase the myocardial force of contraction is strictly related to their cardenolide structure having a 17β-lactone on a 14-hydroxy-5β,14β-androstane skeleton.

In the field of 5α,14α-androstane derivatives some groups of compounds are reported to possess positive inotropic properties.

GB 1,175,219 and U.S. Pat. No. 3,580,905 disclose 3-(aminoalkoxycarbonylalkylene) steroid derivatives which possess digitalis-like activities with "a ratio between the dose which produces toxic symptoms (onset of cardiac arrhythmias) and the effective dose comparable with such a ratio as measured for standard cardiac glycosides". Besides no clear advantage over digitalis glycosides, the compounds with the highest ratio produce the lowest increase in contractile force.

6-Hydroxy and 6-oxoandrostane derivatives are disclosed in EP 0 825 197 B1 as ligands and inhibitors of Na$^+$,K$^+$-ATPase, and positive inotropic agents possessing a lower toxicity when compared with digoxin, as evaluated on the basis of the acute toxicity in mice. The same compounds are also reported by S. De Munari, et al., *J. Med. Chem.* 2003, 46(17), 3644-3654.

The evidence that high levels of endogenous ouabain (EO), a closely related isomer of ouabain, are implicated in human hypertension and cardiac hypertrophy and failure stimulated the pharmacological research for developing novel anti-hypertensive agents active as ouabain antagonists. The pathogenetic mechanisms through which increased EO levels affect cardiovascular system involve the modulation of Na—K ATPase, the key enzyme responsible for renal tubular sodium reabsorption and the activation of signaling transduction pathways implicated in growth-related gene transcription. By studying both genetic and experimental rat models of hypertension and comparing them with humans, it has been demonstrated that elevated levels of circulating EO and the genetic polymorphism of the cytoskeletal protein adducin associate with hypertension and high renal Na—K pump activity. Ouabain itself induces hypertension and up-regulates renal Na—K pump when chronically infused at low doses into rats (OS). In renal cultured cells, either incubated for several days with nanomolar concentrations of ouabain or transfected with the hypertensive adducin genetic variant, the Na—K pump results enhanced. Moreover, both EO and adducin polymorphism affect cardiac complications associated to hypertension, the former through the activation of a signalling transduction pathway. As a consequence, a compound able to interact with the cellular and molecular alterations, sustained by EO or mutated adducin, may represent the suitable treatment for those patients in whom these mechanisms are at work (Ferrandi M et al., Curr Pharm Des. 2005; 11(25):3301-5).

As reported above, the crucial point of positive inotropic agents is the ability to discriminate between the potency in inducing an increase of myocardial force of contraction and the onset of cardiac arrhythmias.

There is still a constant need to make available drugs showing a better therapeutic ratio and/or a longer duration of action, both of them important factors for the compliance of patients. Preferably, such drugs should be suitable for oral administration.

Different steroids, with the B ring enlarged and/or with one carbon atom replaced by a heteroatom, are reported to possess different pharmacological activities as well as some action on the Na$^+$,K$^+$-ATPase or as diuretics.

3-Hydroxy and 3-keto B-homoandrostane derivatives are disclosed in JP 45023140, as anabolic and antiandrogenic steroids, and in U.S. Pat. No. 3,059,019 and by H. J. Ringold in *J. Am. Chem. Soc.*, 1960, 82, 961-963, as anabolic and antigonadotrophic compounds.

Natural or synthetic brassinolides (2,3-dihydroxy-6-keto-7-oxa-7a-homo derivatives) are reported to be plant growth regulators (CS 274530) and some of them are inhibitors or stimulators of Na$^+$,K$^+$-ATPase (L. Starka, et al., Sbornik Lekarski, 1997, 98, 21-25).

6-Azaestranes are claimed in U.S. Pat. No. 3,328,408 as diuretic and hypoglycemic agents and hence useful in the treatment of congestive heart failure.

Compounds resembling steroidal structures with an oxygen atom in the B ring are reported by R. K. Razdan et al. in *J. Med. Chem.*, 1976, 19, 719-721, as inactive or almost inactive agents in hypertensive rats, even though their dosage was quite high (10 mg/kg).

DESCRIPTION OF THE INVENTION

It has now been found that 3-aminoalkoxyimino derivatives of substituted B-homoandrostanes and B-heteroandrostanes meet the needs of providing drugs with a better therapeutic ratio and/or longer duration of action. The compounds of the present invention have the general formula (I):

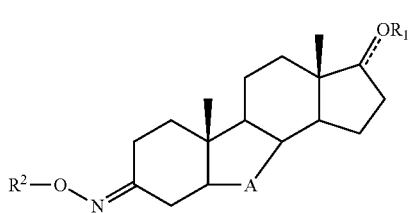

wherein:
A is a divalent group selected among

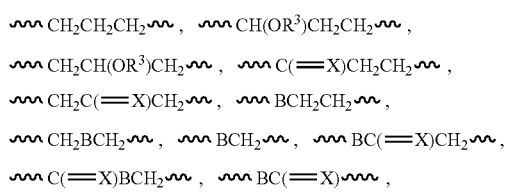

wherein the ⁓ symbols indicate α or β single bonds which connect the A group to the androstane skeleton at position 5 or 8;
B is oxygen or $NR^4$;
$R^3$ is H or $C_1$-$C_6$ alkyl group;
X is oxygen, sulphur or $NOR^5$;
$R^4$ is H, $C_1$-$C_6$ alkyl group, or formyl when A is

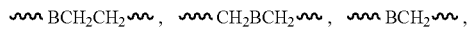

in which B is $NR^4$;
$R^5$ is H or $C_1$-$C_6$ alkyl group;
$R^1$ is H, $C_1$-$C_6$ alkyl group or $C_2$-$C_6$ acyl group when the bond ⁼ in position 17 of the androstane skeleton is a single bond; or
$R^1$ is not present when the bond ⁼ in position 17 is a double bond;
$R^2$ is $DNR^6R^7$ or the group

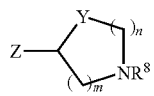

with the groups D or Z linked to the oxygen atom;
D is a $C_2$-$C_6$ linear or branched alkylene or a $C_3$-$C_6$ cycloalkylene, optionally containing a phenyl ring;
$R^6$ and $R^7$, which are the same or different and are H, $C_1$-$C_6$ alkyl, phenyl-$C_1$-$C_4$ alkyl or when $R^6$ is hydrogen; or
$R^7$ is $C(=NR^9)NHR^{10}$; or
$R^6$ and $R^7$, taken together with the nitrogen atom to which they are linked, form an unsubstituted or substituted saturated or unsaturated mono heterocyclic 4-, 5- or 6-membered ring, optionally containing another heteroatom selected from the group consisting of oxygen, sulphur or nitrogen; $R^6$ and $R^7$ are optionally substituted with one or more hydroxy, methoxy, ethoxy groups;
$R^8$ is H, $C_1$-$C_6$ linear or branched alkyl, optionally substituted with one or more hydroxy, methoxy, ethoxy, or $C(=NR^9)NHR^{10}$;

$R^9$ and $R^{10}$, which are the same or different and are H, $C_1$-$C_6$ linear or branched alkyl group; or
$R^9$ and $R^{10}$, taken together with the nitrogen atoms and the guanidinic carbon atom, form an unsubstituted or substituted saturated or unsaturated mono heterocyclic 5- or 6-membered ring optionally containing another heteroatom selected from the group consisting of oxygen, sulphur or nitrogen;
Z is a $C_1$-$C_4$ linear or branched alkylene or a single bond;
Y is $CH_2$, oxygen, sulphur or $NR^{11}$;
$R^{11}$ is H, $C_1$-$C_6$ alkyl group;
n is the number 0 or 1 or 2 or 3;
m is the number 0 or 1 or 2 or 3;
the symbol ⁼ in positions 17 is, independently, a single or double bond, and when it is a single exocyclic bond in positions 17, it is an α or β single bond.

Where the compounds of formula (I) can exhibit tautomerism, the formula is intended to cover all tautomers; the invention includes within its scope all the possible stereoisomers, Z and E isomers, optical isomers (R and S) and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e.g., hydrochloric, hydro-bromic, sulfuric, phosphoric, nitric, fumaric, succinic, oxalic, malic, tartaric, maleic, citric, methanesulfonic or benzoic acid and others commonly used in the art.

The $C_1$-$C_6$ alkyl group may be branched or linear chains or cyclic groups, e.g. methyl, ethyl, n-propyl, i-propyl, n-butyl, t-butyl, cyclopentyl or cyclohexyl.

The $C_2$-$C_6$ alkylenic group may be branched or linear chains, e.g. ethylene, trimethylene, propylene, tetramethylene, methylpropylene, dimethylethylene.

The $C_3$-$C_6$ cycloalkylenic group may be cyclopropylene, cyclobutylene, cyclopentylene, cyclohexylene.

The $C_2$-$C_6$ acyl group may be branched, linear or cyclic chains and preferably are acetyl, propionyl, butyryl, pivaloyl, cyclopentane-carbonyl.

Preferably A is selected among

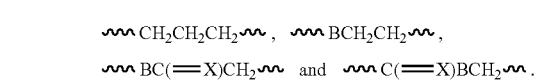

Preferably $R^6$ and $R^7$, which are the same or different, are selected between H and $C_1$-$C_6$ alkyl.

In the context of the present invention metabolite and metabolic precursor means active metabolite and metabolic precursor, namely a compound of formula (I) which has been transformed by a metabolic reaction, but substantially maintains or increases the pharmacological activity.

Examples of metabolites or metabolic precursors are hydroxylated, carboxylated, sulphonated, glycosylated, glycuronated, methylated or demethylated oxidated or reduced derivatives of the compounds of formula (I).

Some compounds of formula (I) can also be prodrugs of the active forms.

Preferred examples of specific compounds (I) of the present invention are:
(E,Z) 3-(2-Aminoethoxyimino)-6-aza-7a-homoandrostane-7,17-dione hydrochloride;

(E,Z) 3-(3-N-Methylaminopropoxyimino)-6-aza-7a-homoandrostane-7,17-dione fumarate;
(E,Z) 3-[3-(R)-Pyrrolidinyl]oxyimino-6-aza-7a-homoandrostane-7,17-dione fumarate;
(E,Z) 3-(2-Aminoethoxyimino)-6-aza-7a-homo-7-thioxoandrostane-17-one hydrochloride;
(E,Z) 3-(2-Aminoethoxyimino)-6-aza-7a-homoandrostane-17-one dihydrochloride;
(E,Z) 3-[3-(R)-Pyrrolidinyl]oxyimino-6-aza-7a-homoandrostane-17-one dihydrochloride;
(E,Z) 3-(2-Aminoethoxyimino)-6-aza-6-formyl-7a-homoandrostane-17-one hydrochloride;
(E,Z) 3-[3-(R)-Pyrrolidinyl]oxyimino-6-aza-6-formyl-7a-homoandrostane-17-one hydrochloride;
3-(E,Z)-(2-Aminoethoxyimino)-6-aza-7a-homo-7-(Z)-hydroxyiminoandrostane-17-one hydrochloride;
3-(E,Z)-(3-N-Methylaminopropoxyimino)-6-aza-7a-homo-7-(Z)-hydroxyimino-androstane-17-one hydrochloride;
3-(E,Z)-[3-(R)-Pyrrolidinyl]oxyimino-6-aza-7a-homo-7-(Z)-hydroxyimino-androstane-17-one hydrochloride;
(E,Z) 3-(2-Aminoethoxyimino)-6-aza-7a-homo-7-(Z)-methoxyimino-androstane-17-one hydrochloride;
3-(E,Z)-[3-(R)-Pyrrolidinyl]oxyimino-6-aza-7a-homo-7-(Z)-methoxyimino-androstane-17-one hydrochloride;
(E,Z) 3-(2-Aminoethoxyimino)-7a-aza-7a-homoandrostane-7,17-dione hydrochloride;
(E,Z) 3-(3-N-Methylaminopropoxyimino)-7a-aza-7a-homoandrostane-7,17-dione hydrochloride;
(E,Z) 3-[3-(R)-Pyrrolidinyl]oxyimino-7a-aza-7a-homoandrostane-7,17-dione hydrochloride;
(E,Z) 3-(2-Aminoethoxyimino)-7a-aza-7a-homoandrostane-17-one difumarate
(E,Z) 3-(3-N-Methylaminopropoxyimino)-7a-aza-7a-homoandrostane-17-one difumarate;
(E,Z) 3-[3-(R)-Pyrrolidinyl]oxyimino-7a-aza-7a-homoandrostane-17-one difumarate;
(E,Z) 3-[3-(R)-Pyrrolidinyl]oxyimino-7a-aza-7a-formyl-7a-homoandrostane-17-one hydrochloride;
(E,Z) 3-(2-Aminoethoxyimino)-6-oxa-7a-homoandrostane-7,17-dione fumarate;
(E,Z) 3-(2-Aminoethoxyimino)-7-oxa-7a-homoandrostane-6,17-dione hydrochloride;
(E,Z)-3-(3-N-Methylaminopropoxyimino)-7-oxa-7a-homoandrostane-6,17-dione hydrochloride;
(E,Z) 3-[3-(R)-Pyrrolidinyl]oxyimino-7-oxa-7a-homoandrostane-6,17-dione hydrochloride;
(E,Z) 3-(2-Aminoethoxyimino)-7a-oxa-7a-homoandrostane-7,17-dione hydrochloride;
(E,Z) 3-(3-N-Methylaminopropoxyimino)-7a-oxa-7a-homoandrostane-7,17-dione hydrochloride;
(E,Z) 3-[3-(R)-Pyrrolidinyl]oxyimino-7a-oxa-7a-homoandrostane-7,17-dione hydrochloride;
(E,Z) 3-(2-Aminoethoxyimino)-7a-oxa-7a-homoandrostane-17-one hydrochloride;
(E,Z) 3-(2-Aminoethoxyimino)-7a-homoandrostane-17-one hydrochloride;
(E,Z) 3-[3-(R)-Pyrrolidinyl]oxyimino-7a-homoandrostane-17-one hydrochloride;
(E,Z) 3-(2-Aminoethoxyimino)-6-oxa-5β-androstan-7,17-dione hydrochloride;
(E,Z) 3-[3-(R)-Pyrrolidinyl]oxyimino-6-azaandrostan-7,17-dione hydrochloride;
(E,Z) 3-(2-Aminoethoxyimino)-B-homoandrostane-17-one hydrochloride;
(E,Z)-3-[3-(R)-Pyrrolidinyl]oxyimino-B-homoandrostane-17-one hydrochloride;
(E,Z)-3-(3-N-Methylaminopropoxyimino)-6-oxa-7a-homoandrostane-7,17-dione fumarate;
(E,Z) 3-[3-(R)-Pyrrolidinyl]oxyimino-6-oxa-7a-homoandrostane-7,17-dione fumarate;
(E,Z)-3-(2-Aminoethoxyimino)-6-oxa-7a-homoandrostane-17-one hydrochloride;
(E,Z)-3-(2-Aminoethoxyimino)-7a-oxa-7a-homoandrostane-17-one hydrochloride;
(E,Z) 3-(2-Aminoethoxyimino)-6-azaandrostane-7,17-dione hydrochloride;
(E,Z) 3-[3-(R)-Pyrrolidinyl]oxyimino-6-azaandrostane-7,17-dione fumarate and the corresponding pure E and Z isomers of the EZ mixtures reported above and the S diastereoisomers of the R diastereoisomers reported above as well as the RS mixtures.

In particular the following pure E and Z isomers have been prepared:

(E) 3-(2-Aminoethoxyimino)-6-aza-7a-homoandrostane-7,17-dione fumarate;
(Z) 3-(2-Aminoethoxyimino)-6-aza-7a-homoandrostane-7,17-dione fumarate;
(Z) 3-(2-Aminoethoxyimino)-6-aza-6-methyl-7a-homoandrostane-7,17-dione hydrochloride
and
(E) 3-(2-Aminoethoxyimino)-6-aza-6-methyl-7a-homoandrostane-7,17-dione hydrochloride.

The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures.

The invention furthermore provides a process for the preparation of compounds of general formula (I) starting from compounds of general formula (II)

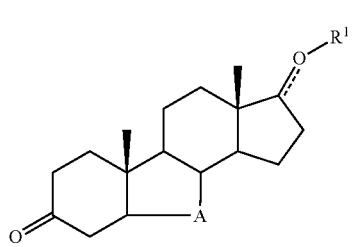

where the symbols A, $R^1$, and ⎓ have the meanings defined above by reaction with compounds of general formula (III)

where $R^2$ has the meaning defined above, in the form of the free base or of a salt, such as, for example, dihydrochloride, in a polar solvent, such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction can be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (I) where the symbols A, $R^1$ and ═══ have the meanings defined above, and $R^2$ is $DNR^6R^7$ or the group

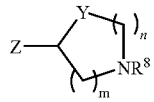

where $R^7$ or $R^8$ are $C(=NR^9)NHR^{10}$, where $R^9$ and $R^{10}$ have the meanings reported above, can be obtained from the corresponding compounds of general formula (I) where $R^6$ and $R^8$ are hydrogen, by reaction with compounds of general formula (IV)

$$TC(=NR^9)NHR^{10} \qquad (IV)$$

where $R^9$ and $R^{10}$ have the meanings reported above and T is a leaving group, such as, for example, methylthio or 1-pyrazolyl. The reaction can be carried out in a solvent such as dioxane, tetrahydrofuran, 1,2-dimethoxyethane, methanol, ethanol, N,N-dimethylformamide, water or their mixtures, at a temperature ranging from 0° C. and the reflux temperature, optionally in the presence of a base, such as sodium or potassium hydroxide, triethylamine, diethylisopropylamine.

Compounds of general formula (II), as defined above, can be prepared starting from known compounds with proper functionality in the different positions, from commercially available compounds, such as, for example, 3β,17β-dihydroxyandrost-5-en-7-one and 3β-hydroxyandrost-5-en-7,17-dione or from compounds already reported in the literature, such as, for example, 3,3:17,17-bis(ethylendioxy)androstan-6-one, 6α-hydroxyandrostane-3,17-dione (both reported in S. De Munari et al, *J. Med. Chem.*, 2003, 46(17), 3644), or 3,3:17,17-bis(ethylendioxy)androst-5-en-7-one (reported by Pui-Kai Li and R. W. Brueggemeier, *J. Med. Chem.* 1990, 33, 101-105), following the general procedures listed below. The above reported list of compounds is an example, not limiting the scope of the invention, of reported methods of preparation of compounds (II).

Compounds of general formula (II), where A is

and X is oxygen can be obtained from the corresponding compounds where A is

is transformed to the corresponding cyanohydrin, followed by reduction to the amino alcohol and final diazotation of the latter.

The cyanohydrin can be obtained by reaction with sodium or potassium cyanide in the presence of an acid, such as sulphuric acid or acetic acid, in a solvent, such as ethanol, dioxane, dimethylsulfoxide, water or one of their mixtures, at a temperature ranging form 0° C. to room temperature, or by treatment of the ketone with another cyanohydrin, such as acetone cyanohydrin, in the presence of a base, such as sodium or potassium hydroxide, in a solvent, such as ethanol, dioxane, dimethylsulfoxide, water or one of their mixtures, or in the cyanohydrin itself as a solvent, at a temperature ranging form 0° C. to room temperature. The cyanohydrin can also be obtained by treatment with cyanotrimethylsilane in the presence of a Lewis acid or base followed by hydrolysis of the silyl ether.

The reduction of the cyanohydrin to the corresponding amino alcohol can be carried out by catalytic hydrogenation, either with hydrogen gas or in hydrogen transfer conditions, in the presence of a metal catalyst, such as Pd/C, $PtO_2$, Pt, Pt/C, or Raney Nickel. Ammonium formate, sodium hypophosphite or cyclohexadiene can be used as hydrogen transfer reagents. The reaction can be carried out in a solvent, such as, for example, ethanol, methanol, ethyl acetate, dioxane, tetrahydrofuran, acetic acid, N,N-dimethylformamide, water or their mixtures, at a temperature ranging from 0° C. and the reflux temperature, at a pressure ranging from atmospheric pressure to 10 atm. The reduction of the cyanohydrin can also be carried out with a reducing agent, such as lithium aluminumhydride in an inert solvent, such as diethyl ether, tetrahydrofuran or dioxane, at a temperature ranging from 0° C. and the reflux temperature.

The diazotation reaction of the amino alcohol to the desired compounds of general formula (II), where A is

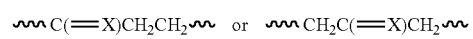

and X is oxygen, can be carried out with sodium or potassium nitrite in the presence of an acid, such as sulphuric, hydrochloric or acetic acid, in a solvent, such as ethanol, dioxane, dimethylsulfoxide, water or one of their mixtures, at a temperature ranging form 0° C. to room temperature.

Compounds of general formula (II), where the substituent A is

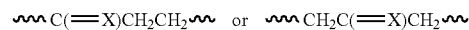

and X is oxygen, can also be obtained from compounds where A is

by treatment with diazomethane or trimethylsilyldiazomethane, in the presence of a Lewis acid, such as $BF_3 \cdot Et_2O$, in a solvent, such as diethyl ether, tetrahydrofuran or dichloromethane, at a temperature ranging from −70° C. and the reflux temperature.

Compounds of general formula (II), where A is

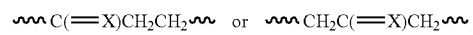

and X is sulphur can be obtained from compounds where A is

and X is oxygen by reaction with the Lawesson reagent or $P_2S_5$, in a solvent, such as toluene or acetonitrile, at a temperature ranging from 0° C. and the reflux temperature.

Compounds of general formula (II), where the substituent A is

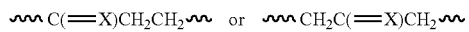

and X is $NOR^5$ can be obtained by treatment of compounds of general formula (II), where A is

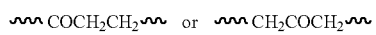

with compounds of general formula $H_2NOR^5$ where $R^5$ is, as defined above, in the form of the free base or of a salt, such as, for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where the substituent A is

can be obtained from compounds where A is

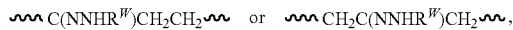

in which $R^W$ is H, $C_6H_5$, tosyl by treatment with a base, such as sodium or potassium hydroxide, sodium or potassium ethoxide in a solvent, such as ethanol, butanol, pentanol, 1,2-ethanediol, or with Na in an alcohol, potassium tert-buthoxide in DMSO, at a temperature ranging from 0° C. and the reflux temperature. The same reaction can be performed with reducing agents, such as lithium aluminum hydride in tetrahydrofuran, sodium cyanoborohydride in methanol or ethanol, optionally in the presence of a Lewis acid, such as zinc chloride, or sodium borohydride in methanol or ethanol, at a temperature ranging from 0° C. and the reflux temperature.

Compounds where A is

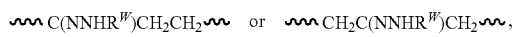

in which $R^w$ is H, $C_6H_5$, tosyl can be obtained by reaction of compounds of general formula (II) where A is

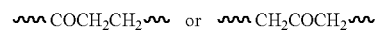

with compounds of general formula $H_2NNR^W$ as a solvent or in a solvent, such as ethanol, dioxane, dimethylsulfoxide, water or one of their mixtures, at a temperature ranging from 0° C. to reflux temperature.

Compounds of general formula (II), where the substituent A is

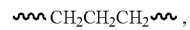

can be obtained from compounds where A is

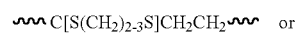

by catalytic hydrogenation, for example, with Raney-Nickel in a solvent such as ethanol, water or dioxane or their mixtures, at a temperature ranging form 0° C. to reflux temperature. Compounds where A is

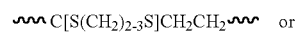

can be obtained by reaction of compounds of general formula (II) where A is

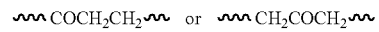

with $HS(CH_2)_{2-3}SH$ and a Lewis acid, such as $BF_3.Et_2O$, in a solvent, such as diethyl ether, tetrahydrofuran or dioxane, at a temperature ranging from 0° C. and the reflux temperature.

Compounds of general formula (II), where the substituents A is

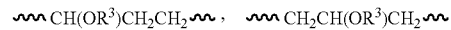

and $R^3$ is hydrogen, can be obtained from compounds of general formula (II), where A is

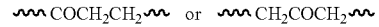

by reduction with a metal hydride, for example, sodium borohydride or lithium aluminiumhydride, in a compatible solvent, such as methanol, ethanol, water for the former reagent and diethyl ether or tetrahydrofuran for the latter, with sodium in an alcohol, such as ethanol or propanol, or by catalytic hydrogenation, such as Pd/C, $PtO_2$, Pt, Pt/C, or Raney Nickel, in a solvent, such as, for example, ethanol, methanol, ethyl acetate, dioxane, tetrahydrofuran, acetic acid, N,N-dimethylformamide, water or their mixtures. All said reactions can be carried out at a temperature ranging from 0° C. and the reflux temperature, at a pressure ranging from atmospheric pressure to 10 atm.

Compounds of general formula (II), where the substituents A is

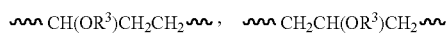

and $R^3$ is $C_1$-$C_6$ alkyl group, can be obtained from compounds of general formula (II), where A is

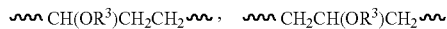

and $R^3$ is hydrogen, with compounds of general formula $R^3$-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (II), where the substituent A is

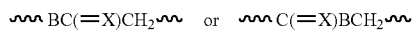

and B and x are oxygen can be obtained by treatment of the corresponding

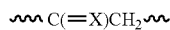

derivatives with peroxides, such as hydrogen peroxide or peroxyacids, such as m-chloroperbenzoic acid, peroxotrifluoroacetic acid or peroxoacetic acid. The reaction can be carried out in a solvent such as, for example, dichloromethane, chloroform, toluene or their mixtures, at a temperature ranging from 0° C. and the reflux temperature, optionally in the presence of a buffer, such as disodium hydrogenphosphate. Compounds of general formula (II), where the substituent A is

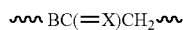

and B and X are oxygen can also be obtained by treatment of a 5-keto-6-acid B seco androstane derivatives with sodium borohydride followed by an acidic treatment. 5-Keto-6-acid B seco androstane derivatives can be obtained by treatment of 5-androstene derivatives with ozone or potassium permanganate or sodium periodate.

Compounds of general formula (II), where the substituent A is

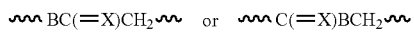

B is $NR^4$ where $R^4$ is hydrogen and X is oxygen can be obtained by treatment of 6- or 7-hydroxyiminoandrostane derivatives with, for example, $SOCl_2$, 2,4,6-trichloro-1,3,5-triazine, tosyl chloride, $P_2O_5$, $POCl_3$, $H_2SO_4$ in a solvent, such as toluene, dichloromethane, pyridine, depending on the nature of the reagent, or the reagent can be used as a solvent, at a temperature ranging from 0° C. and the reflux temperature, optionally followed by a treatment with a base, such as sodium or potassium hydroxide, sodium or potassium carbonate, sodium or potassium hydrogencarbonate, triethylamine, pyridine, in a solvent, such as methanol, ethanol or water or a mixture of the said solvents, at a temperature ranging from room to reflux temperature.

Compounds of general formula (II), where the substituent A is

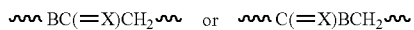

B is $NR^4$ where $R^4$ is $C_1$-$C_6$ alkyl group and X is oxygen can be obtained by treatment of the corresponding compounds of general formula (II), where the substituent A is

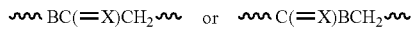

B is $NR^4$ where $R^4$ is hydrogen and X is oxygen, with compounds of general formula $R^4$-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (II), where the substituent A is

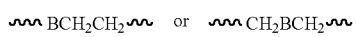

and B is oxygen can be obtained from compounds of general formula (II), where the substituent A is

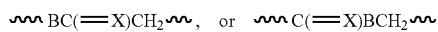

and B and X are oxygen by reduction with mixed hydrides, such as for example, with sodium borohydride or lithium aluminiumhydride in the presence of a Lewis acid, such as $BF_3.Et_2O$, in a solvent, such as diethyl ether, tetrahydrofuran or dioxane, or catalytic hydrogenation over Pd/C in an alcohol, at a temperature ranging from 0° C. and the reflux temperature.

Compounds of general formula (II), where the substituent A is

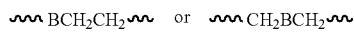

and B is O can be obtained from compounds of general formula (II), where the substituent A is

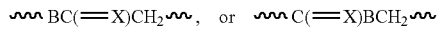

and B and X are oxygen by reduction with mixed hydrides to give the corresponding diol which can be converted to the desired ethers by treatment with tosyl chloride or thionyl chloride in the presence of a base, such as pyridine, triethylamine, 4-dimethylaminopyridine, in a solvent, such as diethyl ether, toluene, dichloromethane, pyridine at a temperature ranging from 0° C. and the reflux temperature.

Compounds of general formula (II), where A is

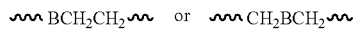

wherein B is $NR^4$ and $R^4$ is hydrogen or $C_1$-$C_6$ alkyl group, can be obtained from compounds of general formula (II), where A is

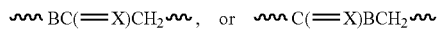

where B is $NR^4$, X is oxygen and $R^4$ is hydrogen or $C_1$-$C_6$ alkyl group, by reduction with mixed hydrides, such as for example, with lithium aluminiumhydride, in a solvent, such as diethyl ether, tetrahydrofuran, dioxane, at a temperature ranging from 0° C. and the reflux temperature.

Compounds of general formula (II), where A is

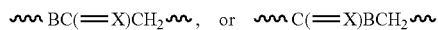

and B is oxygen or $NR^4$, $R^4$ is hydrogen or $C_1$-$C_6$ alkyl group, and X is $NOR^5$ can be obtained from compounds of general formula (II), where A is

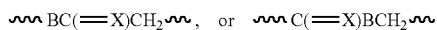

where B is oxygen or $NR^4$, $R^4$ is hydrogen or $C_1$-$C_6$ alkyl group, and X is sulphur by reaction with $H_2NOR^5$ where $R^5$ is as defined above, in the form of the free base or of a salt, such as, for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where A is

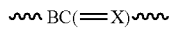

and B and X are oxygen can be obtained from the corresponding compounds where A is

by reaction with $KMnO_4$ or $NaIO_4$ in t-butanol, optionally in the presence of water and bases, such as sodium or hydrogencarbonate, sodium acetate or sodium phosphate, or with $RuCl_3$ or $RuO_2$ and $NaIO_4$ or $NaBrO_3$ in a solvent, such as ethyl acetate, carbontetrachloride, acetonitrile and water or a mixture of the said solvents, at a temperature ranging from 0° C. and the reflux temperature and reduction of the intermediate ketoacid with mild reducing hydrides, for example sodium borohydride followed by cyclization of the intermediate, optionally with catalytic amounts of acids, such as hydrochloric, acetic or p-toluenesulfonic acid.

Compounds of general formula (II), where A is

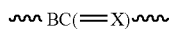

and B is $NR^4$, $R^4$ is hydrogen or $C_1$-$C_6$ alkyl group, and X is oxygen can be obtained from compounds of general formula (II), where A is

by reaction with $KMnO_4$ or $NaIO_4$, in t-butanol, optionally in the presence of water and bases, such as sodium or hydrogencarbonate, sodium acetate or sodium phosphate, or with $RuCl_3$ or $RuO_2$ and $NaIO_4$ or $NaBrO_3$ in a solvent, such as ethyl acetate, carbontetrachloride, acetonitrile and water or a mixture of the said solvents, at a temperature ranging from 0° C. and the reflux temperature, followed by reaction with ammonia, ammonium salt, such as ammonium acetate or formate, or an amine of general formula $H_2NR^4$ to give a carbinol amide. Dehydration of the latter with dehydrating agents, such as thionyl chloride, phosphorous oxychloride, p-toluensulphonic acid and catalytic hydrogenation of the enamide gives compounds of general formula (II), where A is

∿∿BC(=X)∿∿ and B is NR⁴, R⁴ is hydrogen or $C_1$-$C_6$ alkyl group, and X is oxygen.

Compounds of general formula (II), where A is

∿∿BC(=X)∿∿ and B is oxygen or NR⁴, R⁴ is hydrogen or $C_1$-$C_6$ alkyl group, and X is NOR⁵ can be obtained from compounds of general formula (II), where A is

∿∿BC(=X)∿∿ where B is oxygen or NR⁴, R⁴ is hydrogen or $C_1$-$C_6$ alkyl group, and X is sulphur by reaction with $H_2NOR^5$ where R⁵ is as defined above, in the form of the free base or of a salt, such as, for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where the substituent A is

∿∿BCH₂∿∿ and B is oxygen can be obtained from compounds of general formula (II), where the substituent A is

∿∿BC(=X)∿∿ and B and X are oxygen by reduction with mixed hydrides, such as for example, with sodium borohydride or lithium aluminiumhydride in the presence of a Lewis acid, such as $BF_3.Et_2O$, in a solvent, such as diethyl ether, tetrahydrofuran or dioxane, or catalytic hydrogenation over Pd/C in an alcohol, at a temperature ranging from 0° C. and the reflux temperature.

Compounds of general formula (II), where the substituent A is

∿∿BCH₂∿∿ and B is O can also be obtained from compounds of general formula (II), where the substituent A is

∿∿BC(=X)∿∿ and B and X are oxygen by reduction with mixed hydrides to give the corresponding diol which can be converted to the desired ethers by treatment with tosyl chloride or thionyl chloride in the presence of a base, such as pyridine, triethylamine, 4-dimethylaminopyridine, in a solvent, such as diethyl ether, toluene, dichloromethane, pyridine at a temperature ranging from 0° C. and the reflux temperature.

Compounds of general formula (II), where A is

∿∿BCH₂∿∿ and B is NR⁴, wherein R⁴ is hydrogen or $C_1$-$C_6$ alkyl group, can be obtained from compounds of general formula (II), where A

∿∿BC(=X)∿∿ where B is NR⁴, wherein R⁴ is hydrogen or $C_1$-$C_6$ alkyl group, and X is oxygen by reduction with mixed hydrides, such as for example, with lithium aluminiumhydride, in a solvent, such as diethyl ether, tetrahydrofuran dioxane, at a temperature ranging from 0° C. and the reflux temperature.

Compounds of general formula (II), where A is

∿∿BC(=X)CH₂∿∿,  ∿∿C(=X)BCH₂∿∿  or
∿∿BC(=X)∿∿,

B is oxygen or NR⁴, wherein R⁴ is hydrogen or $C_1$-$C_6$ alkyl group, and X is sulphur can be obtained from the corresponding compounds of general formula (II), where A is ∿∿BC(=X)CH₂∿∿,  ∿∿C(=X)BCH₂∿∿  or
∿∿BC(=X)∿∿, wherein B is oxygen or NR⁴, wherein R⁴ is hydrogen or $C_1$-$C_6$ alkyl group, and X is O by reaction with the Lawesson reagent or $P_2S_5$, in a solvent, such as toluene or acetonitrile, at a temperature ranging from 0° C. and the reflux temperature.

Compounds of general formula (II), where A is

∿∿BCH₂∿∿,  ∿∿BCH₂CH₂∿∿,  or  ∿∿CH₂BCH₂∿∿ and B is NR⁴ where R⁴ is formyl can be obtained from compounds of general formula (II), where A is ∿∿BCH₂∿∿,  ∿∿BCH₂CH₂∿∿,  or  ∿∿CH₂BCH₂∿∿ and B is NR⁴ where R⁴ is hydrogen, by a formylation reaction, such as formic acid in acetic anhydride, or formic acid in the presence of a condensing agent, such as N,N'-carbonyldiimidazole, optionally in the presence of a base, such as triethylamine, diethylisopropylamine, 4-dimethylaminopyridine, pyridine, in a solvent, such as dichloromethane, chloroform, acetone, tetrahydrofuran, dioxane, N,N'-dimethylformamide.

In all said transformations, any interfering reactive group can be protected and then deprotected according to well established procedures described in organic chemistry (see for example: T. W. Greene and P. G. M. Wuts "Protective Groups in Organic Synthesis", J. Wiley & Sons, Inc., 3$^{rd}$ Ed., 1999) and well known to those skilled in the art.

All said transformations are only examples of well established procedures described in organic chemistry (see for example: J. March "Advanced Organic Chemistry", J. Wiley & Sons, Inc., 4$^{th}$ Ed., 1992) and well known to those skilled in the art.

Compounds of general formula (III) and (IV) are commercially available or can be prepared from commercially available compounds by standard procedures.

A method of treating a mammal suffering from a cardiovascular disorder, comprising administering a therapeutically effective amount of a compound of Formula (I) as described above represents one of the aspects of the present invention. The term "therapeutically effective amount" as used herein refers to an amount of a therapeutic agent needed to treat, ameliorate a targeted disease or condition, or to exhibit a detectable therapeutic effect.

For any compound, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, drug combination (s), reaction sensitivities, and tolerance/response to therapy. This amount can be determined by routine experimentation and is within the judgement of the clinician. Generally, an effective dose will be from 0.01 mg/kg to 100 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal, rectal means or locally on the diseased tissue after surgical operation.

Dosage treatment may be a single dose schedule or a multiple dose schedule.

Further object of the present invention is the use of said compounds of general formula (I) in the preparation of a medicament useful in the treatment of cardiovascular diseases such as heart failure and hypertension.

Since the compounds of the present invention are shown to be able to antagonize the molecular effects induced by nanomolar ouabain concentrations on the Na—KATPase, they will be effective in the treatment of the diseases caused by the hypertensive effects of endogenous ouabain.

According to a preferred embodiment of the invention the diseases caused by the hypertensive effects of endogenous ouabain include: renal failure progression in autosomal dominant polycystic renal disease (ADPKD), preeclamptic hypertension and proteinuria and renal failure progression in patients with adducin polymorphisms.

In autosomal dominant polycystic renal disease (ADPKD), cyst formation and enlargement are due to cell proliferation and transepithelial secretion of fluids, causing progressive impairment renal function and kidney failure. 1 over 1000 subjects are affected by ADPKD which represents the first genetic cause of renal failure. Renal Na—K ATPase is essential for ion and fluid transport in ADPKD cells and its mislocation and function alteration have been described in this pathology (Wilson P D et al. Am J Pathol 2000; 156:253-268). Ouabain, the inhibitor of the Na—KATPase, inhibits fluid secretion in ADPKD cysts (Grantham J J et al. I Clin. Invest. 1995; 95:195-202) at micromolar concentrations, conversely, at nanomolar concentrations, which are similar to the circulating endogenous ouabain ones, ouabain stimulates ADPKD cell proliferation but does not affect normal human kidney cell growth (Nguyen A N et al. 2007; 18:46-57). It has been demonstrated that ouabain stimulates ADPKD proliferation by binding to the Na—KATPase with high affinity and triggering the activation of the MEK-ERK pathway (Nguyen A N et al. 2007; 18:46-57).

Preeclampsia is a potential devastating disorder of hypertension in pregnancy for which an effective treatment is still lacking. Elevated circulating levels of cardenolides and bufodienolides have been reported in preeclamptic patients and in rat models of the disease (Lopatin D A et al J. Hypertens. 1999; 17:1179-1187; Graves S V et al. Am J Hypertens. 1995; 8:5-11; Adair C D et al. Am J Nephrol. 1996; 16:529-531). The data available suggest that in preeclampsia elevated plasma concentrations of Na—K ATPase inhibitors lead to vasoconstriction and malignant hypertension (Vu H V et al. Am J Nephrol. 2005; 25:520-528). Recently, Digoxin-specific Fab (Digibind) have been proved to reduce blood pressure and increase natriuresis in preeclamptic patients (Pullen M A al. JPET 2004; 310:319-325).

Glomerulosclerosis-associated proteinuria is due to an impairment of the slit-pore structure formed by the podocyte foot-processes in the glomerulus. In particular, slit diaphragm proteins such as nephrin, ZO1, podocyn, synaptopodin and others, in addition to their structural functions participate in common signaling pathways regulated by Fyn a tyrosin kinase of the Src family kinases (Benzing T. J Am Soc Nephrol 2004; 15:1382-1391). Recently, a key role in the structure of the slit pore has been ascribed to beta adducin, a cytoskeletal protein under the control of Fyn (Gotoh H BBRC 2006; 346:600-605; Shima T et al. JBC 2001; 276:42233-42240). Adducin polymorphisms joint to that of ACE have been found associated to impaired renal function in European and Chinese populations (Wang J G et al. J Mol Med 2004; 82:715-722; Wang J G et al. Am J Kidney Dis. 2001; 38:1158-1168). Rostafuroxin and analogues, as endogenous ouabain antagonists, have been described to be able to antagonize the molecular effect of adducin polymorphism on tyrosin kinase signaling (Ferrandi M. et al. JBC, 2004; 279:33306-14; Ferrari et al. Am J Physiol Regul 2006; 290:R529-535; Ferrari P. et al. Med. Hypothes. 2007; 68:1307-1314).

A further object of the present invention are pharmaceutical compositions containing one or more of the compounds of formula (I) described earlier, in combination with excipients and/or pharmacologically acceptable diluents. The compositions in question may, together with the compounds of formula (I), contain known active principles.

A further embodiment of the invention is a process for the preparation of pharmaceutical compositions characterised by mixing one or more compounds of formula (I) with suitable excipients, stabilizers and/or pharmaceutically acceptable diluents.

The invention will now be illustrated in greater detail by means of non-limiting Examples.

EXAMPLES

The following Examples report the synthesis of some compounds of formula (I), whereas the Preparations report the synthesis of useful intermediates.

Example 1

(E,Z) 3-(2-Aminoethoxyimino)-6-aza-7a-homoandrostane-7,17-dione hydrochloride (I-aa)

To a stirred solution of 6-aza-7a-homoandrostane-3,7,17-trione (II-a, Prepn. 1, 1.028 g) in THF (58 mL), a solution of 2-aminoethoxyamine dihydrochloride (0.482 g) and $Na_2HPO_4 \cdot 12H_2O$ (2.32 g) in $H_2O$ (14 mL) was rapidly added dropwise. After 4 h, NaCl (0.5 g) was added and the mixture stirred for 10 min. The phases were separated and the aqueous phase was extracted with THF/tBuOH 1/1 (3×) and then with tBuOH (3×). The combined organic extracts were dried over $Na_2SO_4$, filtered and evaporated to dryness. The crude product was triturated with EtOAc for 4 h and the precipitate was filtered to give the title compound I-aa as a white solid (1.247 g, 93%). $^1$H-NMR (300 MHz, DMSO-$d_6$, ppm from TMS): δ 7.97 (bb, 3H), 7.26 (d, 0.5H), 7.22 (d, 0.5H), 4.09 (m, 2H), 3.52 (m, 1H), 3.15 (m, 0.5H), 3.02 (m, 2H), 2.93 (m, 0.5H), 2.45-1.00 (m, 18H), 0.84 (s, 3H), 0.79 (s, 3H).

Example 2

(E,Z) 3-(2-N-Methylaminoethoxyimino)-6-aza-7a-homoandrostane-7,17-dione fumarate (I-ab)

Prepared in 51% yield as described in Example 1 starting from 6-aza-7a-homoandrostane-3,7,17-trione (II-a, Prepn. 1, 70 mg) and 2-N-methylaminoethoxyamine dihydrochloride (III-a, Prepn. 15, 36 mg). The crude product was purified by flash chromatography ($SiO_2$, $CH_2Cl_2$/MeOH/26% $NH_4OH$ 85/15/1.5). To the concentrated fractions a stoichiometric amount of fumaric acid in MeOH was added. After addition of a 1/1 mixture of EtOAc/$Et_2O$, the precipitate was filtered to give the title compound I-ab as a white solid. $^1$H-NMR (300 MHz, DMSO-$d_6$, ppm from TMS): δ 8.00 (bb, 3H), 7.25 (d, 0.5H), 7.22 (d, 0.5H), 6.40 (s, 2H), 4.09 (m, 2H), 3.49 (m, 1H), 3.11 (m, 0.5H), 3.01 (m, 2H), 2.91 (m, 0.5H), 2.47 (s, 3H), 2.30-1.00 (m, 18H), 0.83 (s, 3H), 0.79 (s, 3H).

Example 3

(E,Z) 3-(3-N-Methylaminopropoxyimino)-6-aza-7a-homoandrostane-7,17-dione fumarate (I-ac)

Prepared in 76% yield as described in Example 1 starting from 6-aza-7a-homo-androstane-3,7,17-trione (II-a, Prepn. 1, 382 mg) and 3-N-methylaminopropoxyamine dihydrochloride (III-b, Prepn. 16, 213 mg). The crude product was purified by flash chromatography ($SiO_2$, $CH_2Cl_2$/MeOH/26% $NH_4OH$ 85/15/1.5). To the concentrated fractions a stoichiometric amount of fumaric acid in MeOH was added. After addition of a 1/1 mixture of EtOAc/$Et_2O$, the precipitate was filtered to give the title compound I-ac. $^1$H-NMR (300 MHz, DMSO-$d_6$, ppm from TMS): δ 8.00 (bb, 3H), 7.21 (d, 0.5H), 7.19 (d, 0.5H), 6.42 (s, 2H), 3.97 (m, 2H), 3.50 (m, 1H), 3.10-2.80 (m, 3H), 2.47 (s, 3H), 2.30-1.00 (m, 20H), 0.83 (s, 3H), 0.79 (s, 3H).

Example 4

(E,Z) 3-[3-(R)-Pyrrolidinyl]oxyimino-6-aza-7a-homoandrostane-7,17-dione fumarate (I-ad)

Prepared in 88% yield as described in Example 1 starting from 6-aza-7a-homoandrostane-3,7,17-trione (II-a, Prepn. 1, 334 mg) and 3-(R)-pyrrolidinyloxyamine dihydrochloride (III-c, Prepn. 17, 171 mg). The crude product was purified by flash chromatography ($SiO_2$, $CHCl_3$/MeOH/26% $NH_4OH$ 85/15/1.5). To the concentrated fractions a stoichiometric amount of fumaric acid in MeOH was added. After addition of a 1/1 mixture of EtOAc/$Et_2O$, the precipitate was filtered to give the title compound I-ad. $^1$H-NMR (300 MHz, DMSO-$d_6$, ppm from TMS): δ 10.00 (bb, 3H), 7.22 (d, 1H), 6.42 (s, 2H), 4.74 (m, 1H), 3.51 (m, 1H), 3.35-3.00 (m, 4.5H), 2.86 (m, 0.5H), 2.50-0.97 (m, 20H), 0.83 (s, 3H), 0.79 (s, 3H).

Example 5

(E,Z) 3-(2-Aminoethoxyimino)-6-aza-6-methyl-7a-homoandrostane-7,17-dione hydrochloride (I-ae)

Prepared in 40% yield as described in Example 1 starting from 6-aza-6-methyl-7a-homoandrostane-3,7,17-trione (II-b, Prepn. 2, 90 mg) and 2-aminoethoxyamine dihydrochloride (40 mg). The phases were separated and the aqueous phase was extracted with THF (3×). The combined organic extracts were dried over $Na_2SO_4$, filtered and evaporated to dryness. The crude product was triturated with $Et_2O$ and the precipitate was filtered to give the title compound I-ae as a white solid. $^1$H-NMR (300 MHz, DMSO-$d_6$, ppm from TMS): δ 7.85 (bb, 3H), 4.10 (m, 2H), 4.03 (m, 1H), 3.06 (m, 3H), 2.80 (m, 1.5H), 2.77 (m, 1.5H), 2.80-1.09 (m, 18H), 0.82 (s, 1.5H), 0.79 (s, 1.5H), 0.78 (s, 1.5H), 0.74 (s, 1.5H)

Example 6

(E) 3-(2-Aminoethoxyimino)-6-aza-6-methyl-7a-homoandrostane-7,17-dione fumarate (I-af)

To a stirred solution of 3-(E)-[2-(9H-fluoren-9-ylmethylcarbonyl)aminoethoxyimino)-6-aza-6-methyl-7a-homoandrostane-7,17-dione (II-c, Prepn. 3, 200 mg) in dry THF (0.96 mL), 1M tetrabutylammonium fluoride in THF (0.390 mL) was added. After stirring at room temperature for 2 h, the solution was concentrated to small volume and purified by flash chromatography ($SiO_2$, $CH_2Cl_2$/MeOH/26% $NH_4OH$ 90/10/1. To the concentrated fractions a stoichiometric amount of fumaric acid in MeOH was added and evaporated to dryness. The crude product was triturated with $Et_2O$ and the precipitate was filtered to give the title compound I-af as a white solid (112 mg, 88%). $^1$H-NMR (300 MHz, DMSO $d_6$, ppm from TMS): δ 8.00 (m, 4H), 6.40 (s, 2H), 4.06 (m, 2H), 4.01 (m, 1H), 2.97 (m, 3H), 2.77 (s, 3H), 2.80-1.09 (m, 18H), 0.78 (s, 3H), 0.73 (s, 3H).

Example 7

(Z)3-(2-Aminoethoxyimino)-6-aza-6-methyl-7a-homoandrostane-7,17-dione hydrochloride (I-ag)

Prepared in 94% yield as described in Example 1 starting from 3-(Z)-[2-(9H-fluoren-9-ylmethylcarbonyl)aminoethoxyimino)-6-aza-6-methyl-7a-homoandrostane-7,17-dione (II-d, Prepn. 3, 160 mg) and 1M tetrabutylammonium fluoride in THF (0.314 mL). The crude product was triturated with $Et_2O$, the precipitate was filtered, dissolved in water and freeze-dried to give the title compound I-ag. $^1$H-NMR (300 MHz, DMSO-$d_6$, ppm from TMS): δ 6.40 (s, 2H), 4.07 (t, 2H), 4.02 (m, 1H), 3.02 (m, 1H), 2.99 (s, 2H), 2.80 (s, 3H), 2.70 (m, 1H), 2.57 (m, 1H), 2.42 (m, 1H), 2.29-1.07 (m, 15H), 0.84 (s, 3H), 0.80 (s, 3H).

Example 8

(E,Z) 3-(3-N-Methylaminopropoxyimino)-6-aza-6-methyl-7a-homoandrostane-7,17-dione hydrochloride (I-ah)

Prepared in 40% yield as described in Example 1 starting from 6-aza-6-methyl-7a-homoandrostane-3,7,17-trione (II-b, Prepn. 2, 90 mg) 3-N-methylaminopropoxyamine dihydrochloride (III-b, Prepn. 16, 40 mg). The phases were separated and the aqueous phase was extracted with THF (3×). The combined organic extracts were dried over $Na_2SO_4$, filtered and evaporated to dryness. The crude product was triturated with $Et_2O$ and the precipitate was filtered to give the title compound I-ah as a white solid. $^1$H-NMR (300 MHz, DMSO-$d_6$, ppm from TMS): δ 8.50 (bb, 2H), 4.10-3.95 (m, 3H), 2.94 (bb, 2H), 2.80 (m, 3H), 2.76-2.61 (m, 2H), 2.56 (s, 3H), 2.46-1.80 (m, 8H), 1.78-1.10 (m, 11H), 0.83 (s, 1.5H), 0.79 (s, 1.5H), 0.78 (s, 1.5H), 0.73 (s, 1.5H).

Example 9

(E,Z) 3-[3-(R)-Pyrrolidinyl]oxyimino-6-aza-6-methyl-7a-homoandrostane-7,17-dione hydrochloride (I-ai)

Prepared in 40% yield as described in Example 1 starting from 6-aza-6-methyl-7a-homo-androstane-3,7,17-trione (II-b, Prepn. 2, 80 mg) and 3-(R)-pyrrolidinyloxy amine dihydrochloride (III-c, Prepn. 17, 42 mg). The combined organic extracts were dried over $Na_2SO_4$, filtered and evaporated to dryness. The crude product was dissolved in water and freeze-dried to give the title compound I-ai as a white solid. $^1$H-NMR (300 MHz, DMSO-$d_6$, ppm from TMS): δ 9.42 (bb, 2H), 4.77 (m, 1H), 4.12 (m, 0.5H), 4.04 (m, 0.5H), 3.30-3.06 (m, 4.5H), 2.98 (m, 0.5H), 2.80 (s, 1.5H), 2.77 (s, 1.5H), 2.82-1.10 (m, 20H), 0.83 (s, 1.5H), 0.79 (s, 1.5H), 0.78 (s, 1.5H), 0.73 (s, 1.5H)

Example 10

(E,Z) 3-(2-Aminoethoxyimino)-6-aza-7a-homo-7-thioxoandrostane-17-one hydrochloride (I-aj)

Prepared in 76% yield as described in Example 1 starting from 6-aza-7a-homo-7-thioxoandrostane-3,17-dione (II-e, Prepn. 4, 75 mg) and 2-aminoethoxyamine dihydrochloride (33 mg). The phases were separated and the aqueous phase was extracted with THF (3×). The combined organic extracts were dried over $Na_2SO_4$, filtered and evaporated to dryness. The crude product was triturated with $Et_2O$ and the precipitate was filtered to give the title compound I-aj as a white solid. $^1$H-NMR (300 MHz, DMSO-$d_6$, ppm from TMS): δ 9.76 (d, 0.5H), 9.72 (d, 0.5H), 7.91 (bb, 3H), 4.09 (m, 2H), 3.85 (m, 1H), 3.23 (m, 0.5H), 3.04 (m, 2H), 2.93 (m, 0.5H), 2.85-1.04 (m, 18H), 0.85 (s, 3H), 0.80 (s, 3H).

Example 11

(E,Z) 3-(2-Aminoethoxyimino)-6-aza-7a-homoandrostane-17-one dihydrochloride (I-ak)

To a stirred solution of 6-aza-7a-homoandrostane-3,17-dione (II-f, Prepn. 5, 75 mg) in dioxane (1 mL), a solution of 2-aminoethoxyamine dihydrochloride (33 mg) in water (1 mL) was rapidly added dropwise. After 3 h the mixture was freeze-dried and the residue was triturated with $Et_2O$ for 5 h and the precipitate was filtered. The crude product was dissolved in water and freeze-dried to give the title compound I-ak as a white solid (89 mg, 83%). $^1$H-NMR (300 MHz, DMSO-$d_6$, ppm from TMS): δ 9.87 (bb, 0.5H), 9.54 (bb, 0.5H), 8.40 (bb, 1H), 8.15 (bb, 1.5H), 8.06 (bb, 1.5H), 4.13 (m, 2H), 3.56 (m, 0.5H), 3.30-2.94 (m, 5H), 2.85 (m, 0.5H), 2.73-1.03 (m, 18H), 1.10 (s, 1.5H), 1.08 (s, 1.5H), 0.79 (s, 3H).

Example 12

(E,Z) 3-(3-N-Methylaminopropoxyimino)-6-aza-7a-homoandrostane-17-one difumarate (I-al)

Prepared in 70% yield as described in Example 1 starting from 6-aza-7a-homoandrostane-3,17-dione (II-f, Prepn. 5, 74 mg) and 3-N-methylaminopropoxyamine dihydrochloride (III-b, Prepn. 16, 39 mg). The crude product was purified by flash chromatography ($SiO_2$, $CH_2Cl_2$/MeOH/26% $NH_4OH$ 85/15/1.5). To the concentrated fractions a stoichiometric amount of fumaric acid in MeOH was added. After addition of $Et_2O$, the precipitate was filtered to give the title compound I-al as a white solid. $^1$H-NMR (300 MHz, DMSO-$d_6$, ppm from TMS): δ 9.00 (bb, 6H), 6.46 (s, 4H), 3.96 (m, 2H), 3.20-2.70 (m, 6H), 2.50 (s, 3H), 2.50-0.82 (m, 20H), 0.94 (s, 3H), 0.78 (s, 3H).

Example 13

(E,Z) 3-[3-(R)-Pyrrolidinyl]oxyimino-6-aza-7a-homoandrostane-17-one dihydrochloride (I-am)

Prepared in 90% yield as described in Example 1 starting from 6-aza-7a-homo-androstane-3,7,17-trione (II-f, Prepn. 5, 76 mg) and 3-(R)-pyrrolidinyloxyamine dihydrochloride (III-c, Prep. 17, 39 mg). $^1$H-NMR (300 MHz, DMSO-$d_6$, ppm from TMS): δ 9.77 (bb, 1H), 9.33 (bb, 2H), 8.27 (bb, 1H), 4.79 (m, 1H), 3.64-1.00 (m, 28H), 1.09 (s, 1.5H), 1.08 (s, 1.5H), 0.79 (s, 3H).

Example 14

(E,Z) 3-(2-Aminoethoxyimino)-6-aza-6-formyl-7a-homoandrostane-17-one hydrochloride (I-an)

Prepared in 90% yield as described in Example 1 starting from 6-aza-6-formyl-7a-homoandrostane-3,17-dione (II-g, Prepn. 6, 80 mg) and 2-aminoethoxyamine dihydrochloride (38 mg). The crude product was triturated with Et$_2$O and the precipitate was filtered to give the title compound I-an as a white solid. $^1$H-NMR (300 MHz, DMSO-$d_6$, ppm from TMS): δ 8.40-7.40 (m, 4H), 4.09 (m, 2H), 3.95-0.72 (m, 24H), 0.93 (s, 1.5H), 0.88 (s, 1.5H), 0.75 (s, 3H).

Example 15

(E,Z) 3-(3-N-Methylaminopropoxyimino)-6-aza-6-formyl-7a-homoandrostane-17-one hydrochloride (I-ao)

Prepared in 50% yield as described in Example 1 starting from 6-aza-6-formyl-7a-homoandrostane-3,17-dione (II-g, Prepn. 6, 80 mg) and 3-N-methylaminopropoxyamine dihydrochloride (III-b, Prepn. 16, 42 mg). The crude product was triturated with Et$_2$O and the precipitate was filtered to give the title compound I-ao as a white solid. $^1$H-NMR (300 MHz, DMSO-$d_6$, ppm from TMS): δ 8.37 (s, 0.5H), 8.34 (bb, 2H), 8.32 (s, 0.5H), 3.99 (t, 2H), 3.80 (m, 1H), 3.55 (m, 1H), 3.05-2.82 (m, 4H), 2.72 (t, 1H), 2.52 (s, 3H), 2.46-0.98 (m, 19H), 0.92 (s, 1.5H), 0.87 (s, 1.5H), 0.74 (s, 3H).

Example 16

(E,Z) 3-[3-(R)-Pyrrolidinyl]oxyimino-6-aza-6-formyl-7a-homoandrostane-17-one hydrochloride (I-ap)

Prepared in 78% yield as described in Example 1 starting from 6-aza-6-formyl-7a-homoandrostane-3,17-dione (II-g, Prepn. 6, 100 mg) and 3-(R)-pyrrolidinyloxyamine dihydrochloride (III-c, Prepn. 17, 53 mg). The crude product was triturated with Et$_2$O and the precipitate was filtered to give the title compound I-ap as a white solid. $^1$H-NMR (300 MHz, DMSO-$d_6$, ppm from TMS): δ 9.00-8.00 (m, 3H), 4.75 (m, 1H), 3.95-0.70 (m, 28H), 0.92 (s, 1.5H), 0.87 (s, 1.5H), 0.75 (s, 3H).

Example 17

3-(E,Z)-(2-Aminoethoxyimino)-6-aza-7a-homo-7-(Z)-hydroxyiminoandrostane-17-one hydrochloride (I-aq)

Prepared in 40% yield as described in Example 1 starting from 6-aza-7a-homo-7-(Z)-hydroxyiminoandrostane-3,17-dione (II-h, Prepn. 7, 100 mg) and 2-aminoethoxyamine dihydrochloride (44 mg). The crude product was triturated with Et$_2$O and the precipitate was filtered to give the title compound I-aq as a white solid. $^1$H-NMR (300 MHz, DMSO-$d_6$, ppm from TMS): δ 9.11 (bb, 1H), 7.97 (bb, 3H), 5.45 (bb, 1H), 4.09 (m, 2H), 3.43 (m, 1H), 3.24 (m, 0.5H), 3.04 (m, 2H), 2.94 (m, 0.5H), 2.52-0.94 (m, 18H), 0.83 (s, 1.5H), 0.82 (s, 1.5H), 0.78 (s, 3H).

Example 18

3-(E,Z)-(3-N-Methylaminopropoxyimino)-6-aza-7a-homo-7-(Z)-hydroxyimino-androstane-17-one hydrochloride (I-ar)

Prepared in 60% yield as described in Example 1 starting from 6-aza-7a-homo-7-(Z)-hydroxyiminoandrostane-3,17-dione (II-h, Prepn. 7, 148 mg) and 3-N-methylaminopropoxyamine dihydrochloride (III-b, Prepn. 16, 79 mg). The crude product was triturated with Et$_2$O and the precipitate was filtered to give the title compound I-ar as a white solid. $^1$H-NMR (300 MHz, DMSO-$d_6$, ppm from TMS): δ 8.90 (bb, 1H), 8.66 (bb, 2H), 5.22 (bb, 1H), 3.98 (m, 2H), 3.40 (m, 1H), 3.10 (m, 0.5H), 2.91 (m, 2H), 2.85 (m, 0.5H), 2.52 (s, 3H), 2.47-0.94 (m, 18H), 0.82 (s, 1.5H), 0.81 (s, 1.5H), 0.78 (s, 3H).

Example 19

3-(E,Z)-[3-(R)-Pyrrolidinyl]oxyimino-6-aza-7a-homo-7-(Z)-hydroxyimino-androstane-17-one hydrochloride (I-as)

Prepared in 60% yield as described in Example 1 starting from 6-aza-7a-homo-7-(Z)-hydroxyiminoandrostane-3,17-dione (II-h, Prepn. 7, 179 mg) and 3-(R)-pyrrolidinyloxyamine dihydrochloride (III-c, Prepn. 17, 94 mg). The crude product was triturated with Et$_2$O and the precipitate was filtered to give the title compound I-as as a white solid. $^1$H-NMR (300 MHz, DMSO-$d_6$, ppm from TMS): δ 9.27 (bb, 2H), 8.93 (bb, 1H), 5.26 (bb, 1H), 4.76 (bb, 1H), 3.43 (m, 1H), 3.06-3.30 (m, 4.5H), 2.87 (m, 0.5H), 2.45 (m, 0.5H), 2.39 (m, 1H), 2.26 (m, 0.5H), 1.90-2.17 (m, 8.5H), 1.82-0.93 (m, 10H), 0.83 (s, 1.5H), 0.82 (s, 1.5H), 0.78 (s, 3H).

Example 20

(E,Z) 3-(2-Aminoethoxyimino)-6-aza-7a-homo-7-(Z)-methoxyimino-androstane-17-one hydrochloride (I-at)

Prepared in 60% yield as described in Example 1 starting from 6-aza-7a-homo-7-(Z)-methoxyiminoandrostane-3,17-dione (II-i, Prepn. 8, 65 mg) and 2-aminoethoxyamine dihydrochloride (28 mg). The crude product was triturated with Et$_2$O and the precipitate was filtered to give the title compound I-at as a white solid. $^1$H-NMR (300 MHz, DMSO-$d_6$, ppm from TMS): δ 7.87 (bb, 3H), 5.31 (bb, 0.5H), 5.28 (bb, 0.5H), 4.08 (m, 2H), 3.57 (s, 3H), 3.21 (m, 0.5H), 3.02 (m, 2H), 2.92 (m, 0.5H), 2.50-0.75 (m, 18H), 0.82 (s, 1.5H), 0.81 (s, 1.5H), 0.78 (s, 3H).

Example 21

3-(E,Z)-[3-(R)-Pyrrolidinyl]oxyimino-6-aza-7a-homo-7-(Z)-methoxyimino-androstane-17-one hydrochloride (I-au)

Prepared in 70% yield as described in Example 1 starting from 6-aza-7a-homo-7-(Z)-methoxyiminoandrostane-3,17- dione (II-i, Prepn. 8, 61 mg) and 3-(R)-pyrrolidinyloxyamine dihydrochloride (III-c, Prepn. 17, 31 mg). The crude product was triturated with Et$_2$O and the precipitate was filtered to give the title compound I-au as a white solid. $^1$H-NMR (300 MHz, DMSO-d$_6$, ppm from TMS): δ 8.72 (bb, 2H), 5.31 (bb, 1H), 4.75 (m, 1H), 3.58 (s, 3H), 3.50-0.90 (m, 26H), 0.82 (s, 1.5H), 0.81 (s, 1.5H), 0.78 (s, 3H).

Example 22

(E,Z) 3-(2-Aminoethoxyimino)-7a-aza-7a-homoandrostane-7,17-dione hydrochloride (I-av)

Prepared in 65% yield as described in Example 1 starting from 7a-aza-7a-homoandrostane-3,7,17-trione (II-j, Prepn. 9, 96 mg) and 2-aminoethoxyamine dihydrochloride (47 mg). The crude product was triturated with Et$_2$O and the precipitate was filtered to give the title compound I-av as a white solid. $^1$H-NMR (300 MHz, DMSO-d$_6$, ppm from TMS): δ 7.97 (bb, 3H), 6.99 (bb, 1H), 4.08 (m, 2H), 3.58 (m, 1H), 3.10-1.75 (m, 3H), 2.50-1.00 (m, 18H), 1.05 (s, 1.5H), 1.04 (s, 1.5H), 0.78 (s, 3H).

Example 23

(E,Z) 3-(3-N-Methylaminopropoxyimino)-7a-aza-7a-homoandrostane-7,17-dione hydrochloride (I-aw)

Prepared in 70% yield as described in Example 1 starting from 7a-aza-7a-homoandrostane-3,7,17-trione (II-j, Prepn. 9, 58 mg) and 3-N-methylaminopropoxyamine dihydrochloride (III-b, Prepn. 16, 32 mg). The crude product was triturated with Et$_2$O and the precipitate was filtered to give the title compound I-aw as a white solid. $^1$H-NMR (300 MHz, DMSO-d$_6$, ppm from TMS): δ 8.50 (bb, 2H), 6.98 (bb, 1H), 3.97 (m, 2H), 3.59 (m, 1H), 2.88 (m, 3H), 2.52 (s, 1.5H), 2.51 (s, 1.5H), 2.50-0.95 (m, 20H), 1.05 (s, 1.5H), 1.04 (s, 1.5H), 0.78 (s, 3H).

Example 24

(E,Z) 3-[3-(R)-Pyrrolidinyl]oxyimino-7a-aza-7a-homoandrostane-7,17-dione hydrochloride (I-ax)

Prepared in 75% yield as described in Example 1 starting from 7a-aza-7a-homoandrostane-3,7,17-trione (II-j, Prepn. 9, 95 mg) and 3-(R)-pyrrolidinyloxyamine dihydrochloride (III-c, Prepn. 17, 32 mg). The crude product was triturated with Et$_2$O and the precipitate was filtered to give the title compound I-ax as a white solid. $^1$H-NMR (300 MHz, DMSO-d$_6$, ppm from TMS): δ 9.04 (bb, 2H), 6.99 (bb, 1H), 4.74 (bb, 1H), 3.58 (bb, 1H), 3.07-3.28 (m, 3H), 2.88 (m, 2H), 2.46-1.31 (m, 18H), 1.09 (m, 2H), 1.05 (s, 1.5H), 1.04 (s, 1.5H), 0.78 (s, 3H).

Example 25

(E,Z) 3-(2-Aminoethoxyimino)-7a-aza-7a-homoandrostane-17-one difumarate (I-ay)

Prepared in 71% yield as described in Example 1 starting from 7a-aza-7a-homoandrostane-3,17-dione (II-k, Prepn. 10, 44 mg) and 2-aminoethoxyamine dihydrochloride (21 mg). After 1.5 h the mixture was freeze-dried and the residue was purified by flash chromatography (SiO$_2$, CH$_2$Cl$_2$/MeOH/26% NH$_4$OH 90/10/1). To the concentrated fractions a stoichiometric amount of fumaric acid in MeOH was added. After addition of Et$_2$O, the precipitate was filtered to give the title compound I-ay as a white solid. $^1$H-NMR (300 MHz, DMSO-d$_6$, ppm from TMS): δ 6.45 (s, 4H), 4.07 (t, 2H), 3.00 (m, 2H), 2.92 (m, 1H), 2.78 (bb, 2H), 2.70 (t, 1H), 2.41 (m, 1H), 2.28-1.20 (m, 10H), 0.94 (m, 2H), 0.93 (s, 1.5H), 1.04 (s, 1.5H), 0.78 (s, 3H).

Example 26

(E,Z) 3-(3-N-Methylaminopropoxyimino)-7a-aza-7a-homoandrostane-17-one difumarate (I-az)

Prepared in 60% yield as described in Example 1 starting from 7a-aza-7a-homoandrostane-3,17-dione (II-k, Prepn. 10, 63 mg) and 3-N-methylaminopropoxyamine dihydrochloride (III-b, Prepn. 16, 37 mg). After 1.5 h the mixture was freeze-dried and the residue was purified by flash chromatography (SiO$_2$, CH$_2$Cl$_2$/MeOH/26% NH$_4$OH 85/15/1.5). To the concentrated fractions a stoichiometric amount of fumaric acid in MeOH was added. After addition of Et$_2$O, the precipitate was filtered to give the title compound I-az as a white solid. $^1$H-NMR (300 MHz, DMSO-d$_6$, ppm from TMS): δ 8.49 (bb, 1H), 8.39 (bb, 2H), 6.61 (s, 4H), 3.96 (t, 2H), 3.47 (bb, 1H), 3.11 (bb, 2H), 2.92 (bb, 2H), 2.89 (bb, 1H), 2.55 (s, 3H), 2.34 (bb, 1H), 2.23-1.30 (m, 18H), 0.96 (s, 1.5H), 0.95 (s, 1.5H), 0.81 (s, 3H).

Example 27

(E,Z) 3-[3-(R)-Pyrrolidinyl]oxyimino-7a-aza-7a-homoandrostane-17-one Difumarate (I-ba)

Prepared in 82% yield as described in Example 1 starting from 7a-aza-7a-homoandrostane-3,17-dione (II-k, Prepn. 10, 93 mg) and 3-(R)-pyrrolidinyloxyamine dihydrochloride (III-c, Prep. 17, 53 mg). After 2 h the mixture was freeze-dried and the residue was purified by flash chromatography (SiO$_2$, CH$_2$Cl$_2$/MeOH/26% NH$_4$OH 83/17/1.7). To the concentrated fractions a stoichiometric amount of fumaric acid in MeOH was added. After addition of Et$_2$O, the precipitate was filtered to give the title compound I-ba as a white solid. $^1$H-NMR (300 MHz, DMSO-d$_6$, ppm from TMS): δ 6.45 (s, 4H), 4.72 (bb, 1H), 3.25 (m, 3H), 3.11 (m, 1H), 2.87 (m, 3H), 2.44 (m, 1H), 2.30-0.99 (m, 20H), 0.94 (s, 3H), 0.79 (s, 3H).

Example 28

(E,Z) 3-(2-Aminoethoxyimino)-7a-aza-7a-formyl-7a-homoandrostane-17-one hydrochloride (I-bb)

Prepared in 75% yield as described in Example 1 starting from 7a-aza-7a-formyl-7a-homoandrostane-3,17-dione (II-l, Prepn. 11, 50 mg) and 2-aminoethoxyamine dihydrochloride (23 mg). The crude product was triturated with Et$_2$O and the precipitate was filtered to give I-bb as a white solid. $^1$H-NMR (300 MHz, DMSO-d$_6$, ppm from TMS): δ 8.12 (s, 1H), 7.86 (bb, 3H), 4.11 (t, 1H), 4.06 (t, 2H), 3.46 (bb, 1H), 3.18 (t, 1H), 3.03 (m, 0.5H), 3.02 (t, 2H), 2.91 (m, 0.5H), 2.35 (m, 1H), 2.72-1.12 (m, 17H), 0.90 (s, 3H), 0.78 (s, 3H).

Example 29

(E,Z) 3-(3-N-Methylaminopropoxyimino)-7a-aza-7a-formyl-7a-homoandrostane-17-one hydrochloride (I-bc)

Prepared in 63% yield as described in Example 1 starting from 7a-aza-7a-formyl-7a-homoandrostane-3,17-dione (II-l, Prepn. 11, 66 mg) and 3-N-methylaminopropoxyamine dihydrochloride (III-b, Prepn. 16, 35 mg). The crude product was triturated with Et$_2$O and the precipitate was filtered to give I-bc as a white solid. $^1$H-NMR (300 MHz, DMSO-d$_6$, ppm from TMS): δ 8.54 (bb, 2H), 8.12 (s, 1H), 4.11 (t, 1H), 3.95 (t, 2H), 3.46 (m, 1H), 3.17 (t, 1H), 2.95 (bb, 0.5H), 2.88 (t, 2H), 2.81 (bb, 0.5H), 2.51 (s, 3H), 2.35 (m, 1H), 2.20-1.05 (m, 20H), 0.89 (s, 3H), 0.78 (s, 3H).

Example 30

(E,Z) 3-[3-(R)-Pyrrolidinyl]oxyimino-7a-aza-7a-formyl-7a-homoandrostane-17-one hydrochloride (I-bd)

Prepared in 65% yield as described in Example 1 starting from 7a-aza-7a-formyl-7a-homoandrostane-3,17-dione (II-l, Prepn. 11, 64 mg) and 3-(R)-pyrrolidinyloxyamine dihydrochloride (III-c, Prepn. 17, 34 mg). The crude product was triturated with Et$_2$O and the precipitate was filtered to give I-bd as a white solid. $^1$H-NMR (300 MHz, DMSO-d$_6$, ppm from TMS): δ 8.96 (bb, 2H), 8.12 (s, 1H), 4.73 (m, 1H), 4.11 (m, 1H), 3.50-3.05 (m, 6H), 2.97 (m, 0.5H), 2.83 (m, 0.5H), 2.40-1.05 (m, 20H), 0.89 (s, 3H), 0.78 (s, 3H).

Example 31

(E,Z) 3-(2-Aminoethoxyimino)-7-oxa-7a-homoandrostane-6,17-dione hydrochloride (I-be)

Prepared in 66% yield as described in Example 1 starting from 7-oxa-7a-homoandrostane-3,6,17-trione (II-m, Prepn. 12, 88 mg) and 2-aminoethoxyamine dihydrochloride (41 mg). The crude product was triturated with Et$_2$O and the precipitate was filtered to give I-be as a white solid. $^1$H-NMR (300 MHz, DMSO-d$_6$, ppm from TMS): δ 7.78 (bb, 3H), 4.29 (t, 1H), 4.13-3.69 (m, 3H), 3.28-3.18 (m, 1H), 3.04 (m, 2H), 2.97 (m, 0.5H) 2.75-2.24 (m, 2.5H), 2.21-1.06 (m, 14H), 0.87 (s, 3H), 0.81 (s, 3H).

Example 32

(E,Z)-3-(3-N-Methylaminopropoxyimino)-7-oxa-7a-homoandrostane-6,17-dione hydrochloride (I-bf)

Prepared in 74% yield as described in Example 1 starting from 7-oxa-7a-homoandrostane-3,6,17-trione (II-m, Prepn. 12, 130 mg) and 3-N-methylaminopropoxyamine dihydrochloride (III-b, Prepn. 16, 72 mg). The crude product was triturated with Et$_2$O and the precipitate was filtered to give I-bf as a white solid $^1$H-NMR (300 MHz, DMSO-d$_6$, ppm from TMS): δ 8.53 (bb, 3H), 4.32 (m, 1H), 4.09-3.94 (m, 3H), 3.29-3.19 (m, 1H), 2.91 (m, 2H), 2.86 (m, 0.5H), 2.68-2.57 (m, 1H), 2.53 (s, 3H) 2.46-2.24 (m, 8.5H), 2.19-1.05 (m, 15H), 0.86 (s, 3H), 0.81 (s, 3H).

Example 33

(E,Z) 3-[3-(R)-Pyrrolidinyl]oxyimino-7-oxa-7a-homoandrostane-6,17-dione hydrochloride (I-bg)

Prepared in 55% yield as described in Example 1 starting from 7-oxa-7a-homoandrostane-3,6,17-trione (II-m, Prepn. 12, 87 mg) and 3-(R)-pyrrolidinyloxyamine dihydrochloride (III-c, Prepn. 17, 48 mg). The crude product was triturated with Et$_2$O and the precipitate was filtered to give I-bg as a white solid. $^1$H-NMR (300 MHz, DMSO-d$_6$, ppm from TMS): δ 9.20 (bb, 1H), 9.12 (bb, 1H) 4.76 (bb, 1H), 4.43-4.21 (m, 1H), 4.13-3.97 (m, 1H), 3.28 (m, 4H), 3.20 (bb, 0.5H) 2.69-2.23 (m, 3H), 2.20-1.08 (m, 16H), 0.87 (s, 3H), 0.81 (s, 3H).

Example 34

(E,Z) 3-(2-Aminoethoxyimino)-6-oxa-7a-homoandrostane-7,17-dione fumarate (I-bh)

Prepared in 56% yield as described in Example 1 starting from 6-oxa-7a-homoandrostane-3,7,17-trione (II-n, Prepn. 12, 60 mg) and 2-aminoethoxyamine dihydrochloride (28 mg). After 20 h, the crude product was purified by flash chromatography (SiO$_2$, CH$_2$Cl$_2$/MeOH/26% NH$_4$OH 93/7/0.7). To the concentrated fractions a stoichiometric amount of fumaric acid in MeOH was added. After addition of Et$_2$O, the precipitate was filtered to give the title compound I-bh as a white solid. $^1$H-NMR (300 MHz, DMSO-d$_6$, ppm from TMS): δ 6.42 (s, 2H), 4.59 (m, 1H), 4.06 (t, 2H), 3.39 (m, 0.5H), 2.98 (t, 2H), 2.92 (bb, 0.5H), 2.41 (m, 2H), 2.31 (bb, 1H), 2.22-1.03 (m, 15H), 0.93 (s, 1.5H) 0.91 (s, 1.5H), 0.80 (s, 3H).

Example 35

(E,Z) 3-(2-Aminoethoxyimino)-7a-oxa-7a-homoandrostane-7,17-dione hydrochloride (I-bi)

Prepared in 58% yield as described in Example 1 starting from 7a-oxa-7a-homoandrostane-3,7,17-trione (II-o, Prepn. 13, 80 mg) and 2-aminoethoxyamine dihydrochloride (37 mg). The crude product was triturated with Et$_2$O and the precipitate was filtered to give I-bi as a white solid. $^1$H-NMR (300 MHz, DMSO-d$_6$, ppm from TMS): δ 7.66 (bb, 3H), 4.72 (t, 1H), 4.06 (t, 2H), 3.14 (m, 1H), 3.02 (m, 2H), 2.99 (m, 0.5H), 2.42 (m, 0.5H), 2.30-1.12 (m, 17H), 1.06 (s, 1.5H) 1.05 (s, 1.5H), 0.79 (s, 3H).

Example 36

(E,Z) 3-(3-N-Methylaminopropoxyimino)-7a-oxa-7a-homoandrostane-7,17-dione hydrochloride (I-bj)

Prepared in 71% yield as described in Example 1 starting from 7a-oxa-7a-homoandrostane-3,7,17-trione (II-o, Prepn. 13, 75 mg) and 3-N-methylaminopropoxyamine dihydrochloride (III-b, Prepn. 16, 41 mg). The crude product was triturated with Et$_2$O and the precipitate was filtered to give I-bj as a white solid. $^1$H-NMR (300 MHz, DMSO-d$_6$, ppm from TMS): δ 4.70 (m, 1H), 3.97 (t, 2H), 3.13 (m, 1H), 2.98-2.84 (m, 3H), 2.54 (s, 3H), 2.44 (m, 1H), 2.28-1.09 (m, 18H), 1.06 (s, 1.5H) 1.05 (s, 1.5H), 0.78 (s, 3H).

Example 37

(E,Z) 3-[3-(R)-Pyrrolidinyl]oxyimino-7a-oxa-7a-homoandrostane-7,17-dione hydrochloride (I-bk)

Prepared in 69% yield as described in Example 1 starting from 7-oxa-7a-homoandrostane-3,7,17-trione (II-o, Prepn. 13, 95 mg) and 3-(R)-pyrrolidinyloxyamine dihydrochloride (III-c, Prepn. 17, 58 mg). The crude product was triturated with Et$_2$O and the precipitate was filtered to give I-bk as a white solid. $^1$H-NMR (300 MHz, DMSO-d$_6$, ppm from TMS): δ 8.89 (bb, 2H), 4.71 (m, 2H), 3.41-3.05 (m, 5H), 2.93 (m, 1H), 2.43 (m, 1H), 2.30-1.09 (m, 18H), 1.06 (s, 1.5H) 1.05 (s, 1.5H), 0.78 (s, 3H).

Example 38

(E,Z) 3-(2-Aminoethoxyimino)-6-oxa-5β-androstane-7,17-dione hydrochloride

Prepared in 30% yield as described in Example 1 starting from 6-oxa-5β-androstane-3,7,17-trione (II-p, Prepn. 14, 360 mg) and 2-aminoethoxyamine dihydrochloride (176 mg). The crude product was triturated with $Et_2O$ and the precipitate was filtered to give I-bl as a white solid. $^1$H-NMR (300 MHz, DMSO-$d_6$, ppm from TMS): δ 7.88 (bb, 3H), 4.41 (bb, 1H), 4.11 (m, 2H), 3.16 (m, 0.5H), 3.05 (m, 2H), 2.76 (m, 1H), 2.70 (m, 0.5H), 2.61-1.93 (m, 5H), 1.74-1.08 (m, 10H), 1.02 (s, 3H), 0.82 (s, 3H).

Example 39

(E) 3-(2-Aminoethoxyimino)-6-aza-7a-homoandrostane-7,17-dione fumarate (I-bm)

A mixture of 3(E)-[2-(9H-fluoren-9-ylmethylcarbonyl) aminoethoxyimino)-6-aza-7a-homo-androstane-7,17-dione (II-q, Prepn. 18, 720 mg) and 1M tetrabutylammonium fluoride in THF (1.49 mL) was stirred at room temperature for 2 h. The solution was concentrated to small volume and purified by flash chromatography (SiO$_2$, CH$_2$Cl$_2$/MeOH/26% NH$_4$OH 86/14/1.4). To the concentrated fractions a stoichiometric amount of fumaric acid in MeOH was added and evaporated to dryness. The crude product was triturated with Et$_2$O and the precipitate was filtered to give the title compound I-bm as a white solid (340 mg, 57%). $^1$H-NMR (300 MHz, D$_2$O, ppm from TMS): δ 7.37 (bb, 1H), 6.66 (s, 2H), 4.25 (m, 2H), 3.76 (m, 1H), 3.30 (m, 2H), 3.01 (m, 1H), 2.69-1.10 (m, 18H), 0.97 (s, 3H), 0.92 (s, 3H).

Example 40

(Z) 3-(2-Aminoethoxyimino)-6-aza-7a-homoandrostane-7,17-dione fumarate (I-bn)

A mixture of 3(Z)-[2-(9H-fluoren-9-ylmethylcarbonyl) aminoethoxyimino)-6-aza-7a-homo-androstane-7,17-dione (II-r, Prepn. 18, 688 mg) and 1M tetrabutylammonium fluoride in THF (1.5 mL) was stirred at room temperature for 2 h. The solution was concentrated to small volume and purified by flash chromatography (SiO$_2$, CH$_2$Cl$_2$/MeOH/26% NH$_4$OH 86/14/1.4). To the concentrated fractions a stoichiometric amount of fumaric acid in MeOH was added and evaporated to dryness. The crude product was triturated with Et$_2$O and the precipitate was filtered to give the title compound I-bn as a white solid (320 mg, 56%). $^1$H-NMR (300 MHz, D$_2$O, ppm from TMS): δ 7.38 (bb, 1H), 6.56 (s, 2H), 4.26 (m, 2H), 3.75 (m, 1H), 3.32 (m, 3H), 2.66-1.16 (m, 18H), 0.97 (s, 3H), 0.92 (s, 3H).

Example 41

(E,Z) 3-(2-Aminoethoxyimino)-B-homoandrostane-17-one hydrochloride (I-bo)

Prepared as described in Example 1 starting from B-homoandrostane-3,17-dione (50 mg, H. J. Ringold, *J. Am. Chem. Soc.* 1960, 961) and 2-aminoethoxyamine dihydrochloride (25 mg). The combined organic extracts were dried over Na$_2$SO$_4$, filtered and evaporated to dryness. The crude product was triturated with EtOAc and the precipitate was filtered to give the title compound I-bo as a white solid (57 mg, 87%). $^1$H-NMR (300 MHz, DMSO-$d_6$, ppm from TMS): δ 7.40 (s, 2H), 4.06 (m, 2H), 3.04 (m, 2H), 2.88 (m, 0.5H), 2.81 (m, 0.5H), 2.44-0.80 (m, 23H), 0.90 (s, 3H), 0.77 (s, 3H).

Example 42

(E,Z)-3-[3-(R)-Pyrrolidinyl]oxyimino-B-homoandrostane-17-one hydrochloride (I-bp)

Prepared as described in Example 1 starting from B-homoandrostane-3,17-dione (50 mg, H. J. Ringold, *J. Am. Chem. Soc.* 1960, 961) and 3-(R)-pyrrolidinyloxyamine dihydrochloride (III-c, Prepn. 17, 58 mg). The combined organic extracts were dried over Na$_2$SO$_4$, filtered and evaporated to dryness. The combined organic extracts were dried over Na$_2$SO$_4$, filtered and evaporated to dryness. The crude product was triturated with Et$_2$O and the precipitate was filtered to give the title compound I-bp as a white solid (96 mg, 69%). $^1$H-NMR (300 MHz, DMSO-$d_6$, ppm from TMS): δ 9.02 (bb, 2H), 4.71 (m, 12H), 3.40-3.05 (m, 4H), 2.81 (m, 0.5H), 2.75 (m, 0.5H), 2.45-0.82 (m, 25), 0.91 (s, 3H), 0.78 (s, 3H).

Example 43

(E,Z)-3-(3-N-Methylaminopropoxyimino)-6-oxa-7a-homoandrostane-7,17-dione fumarate (I-bq)

Prepared in 49% yield as described in Example 1 starting from 6-oxa-7a-homoandrostane-3,7,17-trione (II-n, Prepn. 12, 210 mg) and 3-N-methylaminopropoxyamine dihydrochloride (III-b, 117 mg). After 20 h, the crude product was purified by flash chromatography (SiO$_2$, CH$_2$Cl$_2$/MeOH/ 26% NH$_4$OH 90/10/0.1). To the concentrated fractions a stoichiometric amount of fumaric acid in MeOH was added. After addition of Et$_2$O, the precipitate was filtered to give the title compound I-bq as a white solid. $^1$H-NMR (300 MHz, DMSO-$d_6$, ppm from TMS): δ 6.42 (s, 2H), 4.58 (m, 1H), 3.98 (m, 2H), 3.23 (m, 0.5H), 2.89-1.0 (m, 22.5H), 2.47 (s, 3H), 0.92 (s, 1.5H), 0.91 (s, 1.5H), 0.79 (s, 3H).

Example 44

(E,Z) 3-[3-(R)-Pyrrolidinyl]oxyimino-6-oxa-7a-homoandrostane-7,17-dione fumarate (I-br)

Prepared in 51% yield as described in Example 1 starting from 6-oxa-7a-homoandrostane-3,7,17-trione (II-n, Prepn. 12, 210 mg) and 3(R)-pyrrolidinyloxyamine dihydrochloride (III-c, 117 mg). After 2 h, the crude product was purified by flash chromatography (SiO$_2$, CH$_2$Cl$_2$/MeOH/26% NH$_4$OH 90/10/0.1). To the concentrated fractions a stoichiometric amount of fumaric acid in MeOH was added. After addition of Et$_2$O, the precipitate was filtered to give the title compound I-br as a white solid. $^1$H-NMR (300 MHz, DMSO-$d_6$, ppm from TMS): δ 6.44 (s, 2H), 4.74 (m, 1H), 4.62 (dd, 0.5H), 4.54 (dd, 0.5H), 3.40-1.00 (m, 25H), 0.92 (s, 1.5H) 0.91 (s, 1.5H), 0.79 (s, 3H).

Example 45

(E,Z)-3-(2-Aminoethoxyimino)-6-oxa-7a-homoandrostane-17-one hydrochloride (I-bs)

Prepared as described in Example 1 starting from 6-oxa-7a-homoandrostane-3,17-dione (II-s, Prepn. 19, 35 mg) and 2-aminoethoxyamine dihydrochloride (17 mg). The combined organic extracts were dried over $Na_2SO_4$, filtered and evaporated to dryness. The crude product was triturated with EtOAc and the precipitate was filtered to give the title compound I-bs as a white solid (43 mg, 94%). $^1$H-NMR (300 MHz, DMSO-$d_6$, ppm from TMS): δ 7.87 (bb, 3H), 4.08 (m, 2H), 3.78-3.40 (m, 3H), 3.18 (m, 0.5H), 3.04 (m, 2H), 2.94 (dd, 0.5H), 2.50-1.75 (m, 18H), 0.90 (s, 1.5H), 0.90 (s, 1.5H), 0.79 (s, 3H).

Example 46

(E,Z)-3-(2-Aminoethoxyimino)-7a-oxa-7a-homoandrostane-17-one hydrochloride (I-bt)

Prepared as described in Example 1 starting from 7a-oxa-7a-homoandrostane-3,17-dione (II-t, Prepn. 20, 85 mg) and 2-aminoethoxyamine (41 mg). The combined organic extracts were dried over $Na_2SO_4$, filtered and evaporated to dryness. The crude product was triturated with EtOAc and the precipitate was filtered to give the title compound I-bt as a white solid (80 mg, 72%). $^1$H-NMR (300 MHz, DMSO-$d_6$, ppm from TMS): δ 7.83 (bb, 3H), 4.07 (m, 2H), 3.65-3.35 (m, 3H), 3.02 (m, 2H), 2.46-1.01 (m, 18H), 0.95 (s, 1.5H), 0.94 (s, 1.5H), 0.79 (s, 3H).

Example 47

(E,Z) 3-(2-Aminoethoxyimino)-6-azaandrostane-7,17-dione hydrochloride (I-bu)

Prepared as described in Example 1 starting from 6-azaandrostane-3,7,17-trione (II-u, Prepn. 21, 147 mg) and 2-aminoethoxyamine dihydrochloride (72 mg). The combined organic extracts were dried over $Na_2SO_4$, filtered and evaporated to dryness. The crude product was triturated with EtOAc and the precipitate was filtered to give the title compound I-bu as a white solid (141 mg, 73%). $^1$H-NMR (300 MHz, DMSO-$d_6$, ppm from TMS): δ 7.88 (bb, 3H), 7.46 (s, 0.5H), 7.37 (s, 0.5H), 4.09 (m, 3H), 3.17 (m, 0.5H), 3.04 (m, 3.5H), 2.40-1.00 (m, 16H), 0.90 (s, 3H), 0.82 (s, 3H).

Example 48

(E,Z) 3-[3-(R)-Pyrrolidinyl]oxyimino-6-azaandrostane-7,17-dione fumarate (I-by)

Prepared in 58% yield as described in Example 1 starting from 6-azaandrostane-3,7,17-trione (II-u, Prepn. 21, 55 mg) and 3(R)-pyrrolidinyloxyamine dihydrochloride (III-c, 32 mg). After 2 h 2M NaOH was added and the aqueous phase was extracted with $CH_2Cl_2$ (3×). The combined organic extracts were washed with brine, dried over $Na_2SO_4$ and evaporated to dryness. The residue was dissolved in MeOH and a stoichiometric amount of fumaric acid in MeOH was added. After addition of EtOAc the precipitate was filtered to give the title compound I-by as a white solid. $^1$H-NMR (300 MHz, DMSO-$d_6$, ppm from TMS): δ 7.46 (s, 0.5H), 7.33 (s, 0.5H), 6.42 (s, 2H), 4.72 (m, 1H), 3.30-2.95 (m, 6H), 2.40-1.00 (m, 18H), 0.89 (s, 3H), 0.81 (s, 3H).

Preparation 1

6-Aza-7a-homo-androstane-3,7,17-trione (II-a)

To a stirred solution of 3,3:17,17-bis(ethylendioxy)androstane-6-one (4.5 g) in THF (92 mL), a solution of hydroxylamine hydrochloride (2.4 g), $Na_2HPO_4.12H_2O$ (12.33 g) in $H_2O$ (44.5 mL) was rapidly added dropwise. After 24 the mixture was extracted with EtOAc (3×). The combined organic extracts were washed with brine, dried over $Na_2SO_4$, filtered and evaporated to dryness to give 3, 3:17,17-bis(ethylendioxy)-6(E)-hydroxyiminoandrostane (4.65 g, 100%). $^1$H-NMR (300 MHz, DMSO-$d_6$, ppm from TMS): δ 10.37 (s, 1H), 3.92-3.67 (m, 8H), 3.15 (bb, 1H), 2.16 (m, 1H), 1.95-1.07 (m, 17H), 0.94 (s, 1H), 0.74 (s, 3H), 0.64 (s, 3H).

To a stirred solution of 3, 3:17,17-bis(ethylendioxy)-6(E)-hydroxyiminoandrostane (7.2 g) in pyridine (115 mL) at 0° C., tosyl chloride (10.15 g) was added. After 24 h at room temperature the solution was heated at 40° C. for 48 h. After cooling at room temperature, water (5.5 ml) was added. After 48 h the solution was quenched with 5% aqueous $NaHCO_3$ to pH 8. The solution was evaporated, water (180 mL) was added and the aqueous phase was extracted with $CH_2Cl_2$ (3×80 mL). The combined organic extracts were washed with brine, dried over $Na_2SO_4$ and evaporated to dryness. The crude product was purified by flash chromatography ($SiO_2$, hexane/$Et_2O$ 90/10) to give 3,3:17,17-bis(ethylendioxy)-6-aza-7a-homoandrostane-7-one (6.56 g, 91%). $^1$H-NMR (300 MHz, DMSO-$d_6$, ppm from TMS): δ 7.03 (bb, 1H), 3.93-3.69 (m, 8H), 3.47-3.37 (m, 1H), 2.32 (m, 1H), 1.98-1.10 (m, 17H), 0.76 (s, 3H), 0.72 (s, 3H).

A solution of 3,3:17,17-bis(ethylendioxy)-6-aza-7a-homoandrostane-7-one (2.42 g) and pTSA .$H_2O$ (5.67 g) in acetone (190 mL) and water (19 mL) was stirred at reflux for 2 h. The solution was neutralized by addition of 5% aqueous $NaHCO_3$ and acetone was evaporated. The aqueous phase was extracted with $CH_2Cl_2$ (3×50 mL). The combined organic extracts were washed with brine, dried over $Na_2SO_4$ and evaporated to dryness. The residue was triturated with mixture of EtOAc/$Et_2O$ 40/60 and the precipitate was filtered to give the title compound II-a as a white solid (1.50 g, 95%). $^1$H-NMR (300 MHz, DMSO-$d_6$, ppm from TMS): δ 7.23 (bb, 1H), 3.86-3.73 (m, 1H), 2.64-1.04 (m, 19H), 0.92 (s, 3H), 0.80 (s, 3H).

Preparation 2

6-Aza-6-methyl-7a-homoandrostane-3,7,17-trione (II-b)

To a stirred solution of 3,3:17,17-bis(ethylendioxy)-6-aza-7a-homoandrostane-7-one (Prepn. 1, 1.00 g) in THF under $N_2$ (40 mL) NaH (60% dispersion in mineral oil, 490 mg) was added. After 1 h MeI (1.064 mL) was added. After stirring at room temperature for 1.5 h, the mixture was quenched by addition of $H_2O$ (30 mL) and the aqueous phase was extracted with EtOAc (3×). The combined organic extracts were washed with brine, dried over $Na_2SO_4$ and evaporated to dryness to give 3, 3:17,17-bis(ethylendioxy)-6-aza-6-methyl-7a-homoandrostane-7-one (1.00 g, 97%). $^1$H-NMR (300 MHz, DMSO-$d_6$, ppm from TMS): δ 3.95-3.70 (m, 9H), 2.76 (s, 3H), 2.50 (m, 1H), 2.14-2.00 (m, 2H), 1.94-1.08 (m, 15H), 1.04-0.92 (m, 1H), 0.79 (s, 3H), 0.75 (s, 3H).

6-Aza-6-methyl-7a-homo-androstane-3,7,17-trione (II-b) was prepared in 85% yield from 3,3:17,17-bis(ethylendioxy)-6-aza-6-methyl-7a-homoandrostane-7-one by the procedure described above for the preparation of 6-aza-7a-homo-androstane-3,7,17-trione (Prepn. 1). The combined organic extracts were washed with $H_2O$, dried over $Na_2SO_4$ and evaporated to dryness to give the title compound II-b. $^1$H-NMR (300 MHz, DMSO-$d_6$, ppm from TMS): δ 4.32 (m, 1H), 3.04-2.93 (m, 1H), 2.76 (m, 1H), 2.73 (s, 3H), 2.46-1.05 (m, 17H), 0.83 (s, 3H), 0.79 (s, 3H).

Preparation 3

3(E)-[2-(9H-Fluoren-9-ylmethylcarbonyl)aminoethoxyimino)-6-aza-6-methyl-7a-homo-androstane-7,17-dione (II-c) and 3(Z)-[2-(9H-fluoren-9-ylmethylcarbonyl)-aminoethoxyimino)-6-aza-6-methyl-7a-homoandrostane-7,17-dione (II-d)

To a stirred solution of (E,Z) 3-(2-aminoethoxyimino)-6-aza-6-methyl-7a-homoandrostane-7,17-dione hydrochloride (I-ae) (430 mg, 35/65 ratio) and Et$_3$N (301 µL under N$_2$ in CH$_2$Cl$_2$ (35 mL) at 0° C., 9-fluorenylmethoxycarbonyl chloride (301 mg) was added. After stirring overnight at room temperature, water was added and the mixture extracted with CH$_2$Cl$_2$. The organic phase was washed with 5% NaHCO$_3$ dried over Na$_2$SO$_4$ and evaporated to dryness. The residue was purified by flash chromatography (SiO$_2$; n-hexane/EtOAc 70/30) to give 3(E)-[2-(9H-fluoren-9-ylmethylcarbonyl)aminoethoxyimino)-6-aza-6-methyl-7a-homoandrostane-7,17-dione (II-c, 205 mg, 33%) and 3(Z)-[2-(9H-fluoren-9-ylmethylcarbonyl)aminoethoxyimino)-6-aza-6-methyl-7a-homoandrostane-7,17-dione (II-d, 168 mg, 27%). II-c: $^1$H-NMR (300 MHz, DMSO-d$_6$, ppm from TMS): δ 7.87 (bb, 2H), 7.67 (bb, 2H), 7.45-7.26 (m, 5H), 4.31-4.15 (m, 3H), 4.02-3.80 (m, 3H), 3.27-3.16 (m, 2H), 2.75 (s, 3H), 2.72-2.52 (m, 2H), 2.46-1.78 (m, 7H), 1.68-0.98 (m, 12H), 0.74 (s, 3H), 0.66 (s, 3H). II-d: $^1$H-NMR (300 MHz, DMSO-d$_6$, ppm from TMS): δ 7.88 (bb, 2H), 7.66 (bb, 2H), 7.45-7.27 (m, 5H), 4.34-4.15 (m, 3H), 4.02-3.78 (m, 3H), 3.21 (m, 2H), 2.92 (m, 1H), 2.75 (s, 3H), 2.76-2.35 (m, 3H), 2.82-1.00 (m, 17H), 0.78 (s, 3H), 0.77 (s, 3H).

Preparation 4

6-Aza-7a-homo-7-thioxoandrostane-3,17-dione (II-e)

To a stirred solution of 6-aza-7a-homoandrostane-3,7,17-trione (II-a, Prepn. 1, 52 mg) in toluene (2 mL) Lawesson reagent (40 mg) was added and stirred at room temperature for 3 h. SiO$_2$ was added and the mixture was evaporated to dryness. The residue was purified by flash chromatography (hexane/acetone 65/35) to the title compound II-e (48 mg, 88%). $^1$H-NMR (300 MHz, DMSO-d$_6$, ppm from TMS): δ 9.72 (bb, 1H), 4.13 (m, 1H), 2.91-2.70 (m, 3H), 2.46-2.30 (m, 2H), 2.22 (m, 1H), 2.13-1.89 (m, 4H), 1.80-1.08 (m, 9H), 0.93 (s, 3H), 0.81 (s, 3H).

Preparation 5

6-Aza-7a-homoandrostane-3,17-dione (II-f)

To a stirred solution of 3,3:17,17-bis(ethylendioxy)-6-aza-7a-homoandrostane-7-one (1.175 g) in THF under N$_2$ (35 mL), LiAlH$_4$ (0.607 mg) was added in portions over 5 minutes at room temperature and the mixture was stirred at reflux for 1 h. The suspension was cooled with an ice bath and then quenched by careful addition of H$_2$O (0.6 mL) and 4N NaOH (0.6 mL). The mixture was filtered through a Celite pad and the filter cake was washed with THF (3×10 mL). The filtrate was washed with brine, dried over Na$_2$SO$_4$, evaporated to dryness and the residue was purified by flash chromatography (SiO$_2$, CH$_2$Cl$_2$/MeOH/26% NH$_4$OH 92/8/0.8) to give 3,3:17,17-bis(ethylendioxy)-6-aza-7a-homoandrostane (880 mg, 77%). $^1$H-NMR (300 MHz, DMSO-d$_6$, ppm from TMS): δ 3.87-3.07 (m, 8H), 2.84 (m, 1H), 2.64-2.51 (m, 2H), 1.91-0.99 (m, 19H), 0.76 (s, 3H), 0.75 (s, 3H), 0.67 (m, 1H).

6-Aza-7a-homoandrostane-3,17-dione was prepared in 95% yield from 3,3:17,17-bis(ethylendioxy)-6-aza-7a-homoandrostane by the procedure described above for the preparation of 6-aza-7a-homoandrostane-3,7,17-trione (Prepn. 1). The combined organic extracts were washed with H$_2$O, dried over Na$_2$SO$_4$ and evaporated to dryness to give the title compound II-f. $^1$H-NMR (300 MHz, DMSO-d$_6$, ppm from TMS): δ 2.94-2.76 (m, 2H), 2.63 (m, 1H), 2.46-2.21 (m, 3H), 2.14-1.89 (m, 5H), 1.82-1.02 (m, 11H), 0.97 (s, 3H), 0.84 (m, 1H), 0.79 (s, 3H).

Preparation 6

6-Aza-6-formyl-7a-homoandrostane-3,17-dione (II-g)

A 1 M solution of formic acid in CHCl$_3$ (3.9 mL) was added dropwise to a solution of DCC (403 mg) in CHCl$_3$ at 0° C. The mixture was stirred for further 5 min and then added to an ice-cooled solution of 6-aza-7a-homoandrostane-3,17-dione (II-f, Prepn. 5, 300 mg) in pyridine (2.9 mL). The mixture was then stirred in an ice bath for 1 h. Evaporation of the solvent, followed by addition of EtOAc, gave a precipitate which was removed by filtration and washed with EtOAc. The combined organic extracts were evaporated to dryness and the residue was purified by flash chromatography (SiO$_2$, hexane/acetone 1/1) to the title compound II-g (250 mg, 76%). $^1$H-NMR (300 MHz, DMSO-d$_6$, ppm from TMS): δ 8.29 (s, 1H), 3.81-3.72 (m, 2H), 3.29 (m, 1H), 2.93 (m, 1H), 2.47-0.97 (m, 18H), 0.97 (s, 3H), 0.76 (s, 3H).

Preparation 7

6-Aza-7a-homo-7-(Z)-hydroxyiminoandrostane-3,17-dione (II-h)

3,3:17,17-Bis(ethylendioxy)-6-aza-7a-homo-7-thioxoandrostane was prepared in 62% yield from 3,3:17,17-bis(ethylendioxy)-6-aza-7a-homoandrostane (Prepn. 5, 567 mg) by the procedure described above for the preparation of 6-aza-7a-homo-7-thioxoandrostane-3,17-dione (Prepn. 4). The crude product was purified by flash chromatography (SiO$_2$, hexane/EtOAc 40/60). $^1$H-NMR (300 MHz, DMSO-d$_6$, ppm from TMS): δ 9.55 (bb, 1H), 3.92-3.65 (m, 9H), 2.80-2.58 (m, 2H), 1.99-0.98 (m, 17H), 0.77 (s, 3H), 0.73 (s, 3H).

To a stirred solution of 3,3:17,17-bis(ethylendioxy)-6-aza-7a-homo-7-thioxoandrostane (600 mg) in pyridine (30 mL), hydroxylamine hydrochloride (789 mg) was added. After 48 h at 60° C. the solution was cooled and quenched with 5% aqueous NaHCO$_3$ to pH 8. After evaporation of the solution, water (180 mL) was added and the aqueous phase was extracted with CH$_2$Cl$_2$ (3×80 mL). The combined organic extracts were washed with brine, dried over Na$_2$SO$_4$ and evaporated to dryness. The crude product was purified by flash chromatography (SiO$_2$, CH$_2$Cl$_2$/isopropyl alcol/MeOH 94/3/3) to give 3,3:17,17-bis(ethylendioxy)-6-aza-7a-homo-7-(Z)-hydroxyiminoandrostane (510 mg, 85%). $^1$H-NMR (300 MHz, DMSO-d$_6$, ppm from TMS): δ 8.70 (s, 1H), 4.90 (bb, 1H), 3.94-3.68 (m, 8H), 2.12-1.07 (m, 19H), 0.86 (bb, 1H), 0.75 (s, 3H), 0.70 (s, 3H).

6-Aza-7a-homo-7-(Z)-hydroxyiminoandrostane-3,17-dione was prepared in 95% yield from 3,3:17,17-bis(ethylendioxy)-6-aza-7a-homo-7-(2)-hydroxyminoandrostane (461 mg) by the procedure described above for the preparation of 6-aza-7a-homo-androstane-3,7,17-trione (Prepn. 1). The crude product was purified by flash chromatography (SiO$_2$, CH$_2$Cl$_2$/iPrOH 95/5) to give the title compound II-h (369 mg). $^1$H-NMR (300 MHz, DMSO-d$_6$, ppm from TMS): δ 8.83 (s, 1H), 5.14 (bb, 1H), 3.67 (m, 1H), 2.70 (m, 1H), 2.48-1.90 (m, 9H), 1.81-1.02 (m, 9H), 0.91 (s, 3H), 0.73 (s, 3H).

Preparation 8

6-Aza-7a-homo-7-(Z)-methoxyiminoandrostane-3, 17-dione (II-i)

To a stirred solution of 3,3:17,17-bis(ethylendioxy)-6-aza-7a-homo-7-thioxoandrostane (Prepn. 6) (240 mg) in pyridine (6.5 mL), methoxyamine hydrochloride (380 mg) was added. After 48 h at 60° C. in sealed bomb the solution was cooled and quenched with 5% aqueous NaHCO$_3$ to pH 8. After evaporation of the solution, water (180 mL) was added and the aqueous phase was extracted with CH$_2$Cl$_2$ (3×80 mL). The combined organic extracts were washed with brine, dried over Na$_2$SO$_4$ and evaporated to dryness. The crude product was purified by flash chromatography (SiO$_2$, acetone/hexane 50/50) to give 3,3:17,17-bis(ethylendioxy)-6-aza-7a-homo-7-(Z)-methoxyiminoandrostane (210 mg, 85%). $^1$H-NMR (300 MHz, DMSO-d$_6$, ppm from TMS): δ 4.90 (bb, 1H), 3.96-3.65 (m, 8H), 3.57 (s, 3H), 2.12-1.10 (m, 19H), 0.94-0.80 (m, 1H), 0.75 (s, 3H), 0.70 (s, 3H).

6-Aza-7a-homo-7-(Z)-methoxyiminoandrostane-3,17-dione was prepared in 95% yield from 3,3:17,17-bis(ethylendioxy)-6-aza-7a-homo-7-(Z)-methoxyiminoandrostane (210 mg) by the procedure described above for the preparation of 6-aza-7a-homo-androstane-3,7,17-trione (Prepn. 1). The crude product was purified by flash chromatography (SiO$_2$, hexane/EtOAc 5/95) to give the title compound II-i (176 mg). $^1$H-NMR (300 MHz, DMSO-d$_6$, ppm from TMS): δ 5.32 (bb, 1H), 3.69 (m, 1H), 3.57 (s, 3H), 2.73 (m, 1H), 2.47-1.90 (m, 8H), 1.81-0.99 (m, 10H), 0.90 (s, 3H), 0.79 (s, 3H).

Preparation 9

7a-Aza-7a-homoandrostane-3,7,17-trione (II-j)

A mixture of 3,3:17,17-bis(ethylendioxy)androst-5-ene-7-one (5.99 g) and 10% Pd/C (0.599 g) in dioxane (186 mL) was stirred under H$_2$ at atm pressure for 7 h. The mixture was filtered through Celite and the filtrate evaporated to dryness. The crude product was purified by flash chromatography (SiO$_2$, hexane/EtOAc 75/25). The product was triturated with hexane/Et$_2$O 1/1 and the precipitate was filtered to give 3,3:17,17-bis(ethylendioxy)androstane-7-one (4.06 g, 67%). $^1$H-NMR (300 MHz, DMSO-d$_6$, ppm from TMS): δ 3.94-3.74 (m, 8H), 2.47 (m, 1H), 2.40 (m, 1H), 2.20 (m, 1H), 1.94-1.02 (m, 17H), 1.13 (s, 3H), 0.82 (s, 3H).

3, 3:17,17-Bis(ethylendioxy)-7(E)-hydroxyiminoandrostane was prepared in quantitative yield from 3,3:17,17-bis(ethylendioxy)androstane-7-one (2.20 g) by the procedure described above for the preparation of 3, 3:17,17-bis(ethylendioxy)-6(E)-hydroxyiminoandrostane (Prepn. 1). $^1$H-NMR (300 MHz, DMSO-d$_6$, ppm from TMS): δ 10.17 (s, 1H), 3.88-3.71 (m, 8H), 2.89 (bb, 1H), 2.23-2.05 (m, 2H), 1.89-0.97 (m, 16H), 0.90 (s, 3H), 0.80 (m, 1H), 0.77 (s, 3H).

7(E)-Hydroxyiminoandrostane-3,17-dione was prepared in 59% yield from 3,3:17,17-bis(ethylendioxy)-7(E)-hydroxyiminoandrostane (1.1 g) by the procedure described above for the preparation of 6-aza-7a-homoandrostane-3,7,17-trione (Prepn. 1). The crude product was purified by flash chromatography (SiO$_2$, CH$_2$Cl$_2$/acetone/hexane 20/20/60) to give 7(E)-hydroxyiminoandrostane-3,17-dione (508 mg). $^1$H-NMR (300 MHz, DMSO-d$_6$, ppm from TMS): δ 10.37 (s, 1H), 3.00 (bb, 1H), 2.57-2.30 (m, 5H), 2.15-1.88 (m, 4H), 1.74-0.89 (m, 10H), 1.13 (s, 3H), 0.82 (s, 3H).

7a-Aza-7a-homoandrostane-3,7,17-trione was prepared in 79% yield from 7(E)-hydroxyiminoandrostane-3,17-dione (490 mg) by the procedure described above for the preparation of 3,3:17,17-bis(ethylendioxy)-6-aza-7a-homoandrostane-7-one (Prepn. 1). $^1$H-NMR (300 MHz, DMSO-d$_6$, ppm from TMS): δ 7.00 (bb, 1H), 3.62 (bb, 1H), 2.95-2.82 (m, 1H), 2.54-2.24 (m, 2H), 2.27-1.30 (m, 14H), 1.15 (s, 3H), 1.11 (m, 2H), 0.79 (s, 3H).

Preparation 10

7a-Aza-7a-homoandrostane-3,17-dione (II-k)

3,3:17,17-Bis(ethylendioxy)-7a-aza-7a-homoandrostane-7-one was prepared in 91% yield from 3,3:17,17-bis(ethylendioxy)-7(E)-hydroxyiminoandrostane (Prepn. 9, 640 mg) by the procedure described above for the preparation of 3,3:17,17-bis(ethylendioxy)-6-aza-7a-homoandrostane (Prepn. 1). The crude product was triturated with hexane/Et$_2$O 9/1 to give of 3, 3:17,17-bis(ethylendioxy)-7a-aza-7a-homoandrostane-7-one (583 mg). $^1$H-NMR (300 MHz, DMSO-d$_6$, ppm from TMS): δ 6.74 (bb, 1H), 3.88-3.71 (m, 8H), 3.30 (m, 1H), 2.75-2.65 (m, 1H), 1.99-1.10 (m, 17H), 0.96 (m, 1H), 0.92 (s, 3H), 0.75 (s, 3H).

3,3:17,17-Bis(ethylendioxy)-7a-aza-7a-homoandrostane was prepared in 44% yield from 3,3:17,17-bis(ethylendioxy)-7a-aza-7a-homoandrostane-7-one (296 mg) by the procedure described above for the preparation of 3, 3:17,17-bis(ethylendioxy)-6-aza-7a-homoandrostane (Prepn. 5). The crude product was purified by flash chromatography to give 3,3:17,17-bis(ethylendioxy)-7a-aza-7a-homoandrostane (125 mg). $^1$H-NMR (300 MHz, DMSO-d$_6$, ppm from TMS): δ 3.90-3.60 (m, 8H), 2.74-2.57 (m, 2H), 2.25 (m, 1H), 1.93-1.08 (m, 19H), 0.85 (m, 1H), 0.80 (s, 3H), 0.75 (s, 3H).

7a-Aza-7a-homoandrostane-3,17-dione was prepared in 42% yield from 3,3:17,17-bis(ethylendioxy)-7a-aza-7a-homoandrostane (395 mg) by the procedure described above for the preparation of 6-aza-7a-homoandrostane-3,17-dione (Prepn. 5). The crude product was purified by flash chromatography (SiO$_2$, CH$_2$Cl$_2$/MeOH/26% NH$_4$OH 93/7/0.7) to give the title compound II-k (128 mg). $^1$H-NMR (300 MHz, DMSO-d$_6$, ppm from TMS): δ 2.80-2.60 (m, 2H), 2.45-2.24 (m, 3H), 2.15-1.16 (m, 16H), 1.15-0.93 (m, 2H), 1.05 (s, 3H), 0.79 (s, 3H).

Preparation 11

7a-Aza-7a-formyl-7a-homoandrostane-3,17-dione (II-l)

7a-Aza-7a-formyl-7a-homoandrostane-3,17-dione was prepared in quantitative yield from 7a-aza-7a-homoandrostane-3,17-dione (II-k, Prepn. 10 55 mg) by the procedure described above for the preparation of 6-aza-6-formyl-7a-homoandrostane-3,17-dione (Prepn. 6). The crude product was purified by flash chromatography (SiO$_2$, hexane/acetone 60/40) to give the title compound II-l (60 mg). $^1$H-NMR (300 MHz, DMSO-d$_6$, ppm from TMS): δ 8.13 (s, 1H), 4.15 (m, 1H), 3.52-3.39 (m, 1H), 3.18 (m, 1H), 2.47-1.08 (m, 19H), 0.91 (s, 3H), 0.89 (s, 3H).

Preparation 12

7-Oxa-7a-homoandrostane-3,6,17-trione (II-m) and 6-oxa-7a-homoandrostane-3,7,17-trione (II-n)

To a stirred solution of 6α-hydroxyandrostane-3,17-dione (4.90 g) in pyridine (10 mL) at 0° C., DMAP (94 mg) and Ac$_2$O (4.55 mL) were added. After stirring overnight at room temperature, the solution was evaporated. The residue was treated with water and extracted with EtOAc (2×). The combined organic extracts were washed with brine, dried over Na$_2$SO$_4$, filtered and evaporated to dryness to give 6α-acetoxyandrostane-3,17-dione (5.57 g, 100%). $^1$H-NMR (300 MHz, DMSO-d$_6$, ppm from TMS): δ 4.66 (m, 1H), 2.47-2.33 (m, 2H), 2.30-2.01 (m, 4H), 2.00 (s, 3H), 1.98-1.08 (m, 12H), 1.05 (s, 3H), 1.00 (m, 1H), 0.84 (m, 1H), 0.80 (s, 3H).

To a stirred solution of 6α-acetoxyandrostane-3,17-dione (5.57 g) in MeOH (188 mL), at 0° C. under N$_2$, NaBH$_4$ (615 mg) was added in portions over 15 min. After stirring for 1.5 h at room temperature, the mixture was quenched by careful addition of H$_2$O (200 mL). MeOH was evaporated and the concentrated solution was extracted with EtOAc. The combined organic extracts were washed with brine, dried over Na$_2$SO$_4$ and evaporated to dryness. The mixture was purified by flash chromatography (SiO$_2$, cyclohexane/Et$_2$O/acetone 60/20/20) to give 6α-acetoxyandrostane-3β,17β-diol and 6α-acetoxyandrostane-3α,17β-diol (90/10 mixture, 5.30 g, 95%). $^1$H-NMR (300 MHz, DMSO-d$_6$, ppm from TMS): δ 4.55 (m, 1H), 4.49 (bb, 1H), 4.43 (bb, 1H), 3.41 (m, 1H), 3.28 (m, 1H), 1.97 (s, 3H), 1.88-0.82 (m, 19H), 0.79 (s, 3H), 0.64 (m, 1H), 0.61 (s, 3H).

To a stirred solution of 6α-acetoxyandrostane-3β,17β-diol and 6α-acetoxyandrostane-3α,17β-diol (90/10 mixture, 5.30 g) in DMF (120 mL) at 0° C., imidazole (4.53 g) and tert-butyldimethylchlorosilane (5.02 g) were added. After stirring overnight at room temperature, the mixture was quenched by addition of H$_2$O (150 mL). DMF was evaporated and the concentrated solution was extracted with Et$_2$O. The combined organic extracts were washed with brine, dried over Na$_2$SO$_4$ and evaporated to dryness. The mixture was purified by flash chromatography (SiO$_2$, cyclohexane/Et$_2$O 95/5) to give 3α,17β-di(dimethyltert-butylsilyloxy)-6α-acetoxyandrostane and 3α,17β-di(dimethyltert-butylsilyloxy)-6α-acetoxyandrostane (90/10 mixture, 7.58 g, 87%). $^1$H-NMR (300 MHz, DMSO-d$_6$/acetone-d$_6$, ppm from TMS): δ 4.60 (m, 1H), 3.59 (m, 1H), 3.55 (m, 1H), 1.95 (s, 3H), 1.93-0.88 (m, 20H), 0.85 (m, 20H), 0.68 (s, 3H), 0.68 (m, 1H), 0.03-0.00 (m, 12H).

To a stirred solution of 3β,17β-di(dimethyltert-butylsilyloxy)-6α-acetoxyandrostane and 3α,17β-di(dimethyltert-butylsilyloxy)-6α-acetoxyandrostane (90/10 mixture, 7.58 g) in MeOH/dioxane 1/4 (100 mL), K$_2$CO$_3$ (896 mg) was added. After stirring for 72 h at 40° C., the mixture was quenched by addition of H$_2$O. The organic solvents were evaporated and the concentrated solution was extracted with EtOAc. The combined organic extracts were washed with brine, dried over Na$_2$SO$_4$ and evaporated to dryness to give 3β,17β-di(dimethyltert-butylsilyloxy)androstane-6α-ol and 3α,17β-di(dimethyltert-butylsilyloxy)androstane-6α-ol (90/10 mixture, 6.30 g, 85%). $^1$H-NMR (300 MHz, DMSO-d$_6$, ppm from TMS): δ 4.30 (bb, 1H), 3.55 (bb, 1H), 3.47 (m, 1H), 2.05 (bb, 1H), 1.92-1.73 (m, 2H), 1.68-0.87 (m, 17H), 0.84 (s, 18H), 0.72 (s, 3H), 0.62 (s, 3H), 0.56 (s, 3H), 0.02 (s, 3H), 0.01 (s, 6H), 0.01 (s, 3H).

To a solution of 3β,17β-di(dimethyltert-butylsilyloxy)androstane-6α-ol and 3α,17β-di(dimethyltert-butylsilyloxy)androstane-6α-ol (90/10 mixture, 6.30 g) in CH$_2$Cl$_2$ (60 mL) under N$_2$, NMNO (4.07 g), TPAP (0.412 g) and 4 Å molecular sieves (3.50 g) were added. The mixture was stirred for 2 h and then SiO$_2$ was added. The mixture was purified by flash chromatography (SiO$_2$, n-hexane/Et$_2$O 50/50) to give 3β,17β-di(dimethyltert-butylsilyloxy)-androstane-6-one and 3α,17β-di(dimethyltert-butylsilyloxy)androstane-6-one (90/10 mixture, 6.30 g, 100%). $^1$H-NMR (300 MHz, DMSO-d$_6$, ppm from TMS): δ 3.68 (m, 1H), 3.67-3.57 (m, 1H), 2.38-2.30 (m, 1H), 2.20-2.12 (m, 1H), 1.99-1.05 (m, 18H), 0.90 (s, 9H), 0.88 (s, 9H), 0.75 (s, 3H), 0.74 (s, 3H), 0.07-0.03 (s, 12H).

To a stirred solution of 3β,17β-di(dimethyltert-butylsilyloxy)androstane-6-one and 3α,17β-di(dimethyltert-butylsilyloxy)androstane-6-one (mixture 90/10, 660 mg) in CH$_2$Cl$_2$ (10 mL), at 0° C., 3-chloroperbenzoic acid (~70%, 1.20 g) was added in portions over 15 min. After stirring for 72 h at room temperature, the mixture was quenched by careful addition of 5% K$_2$CO$_3$ aqueous solution (200 mL). The organic layer was washed with Na$_2$SO$_3$ solution, brine, dried over Na$_2$SO$_4$ and evaporated to dryness. The mixture was purified by flash chromatography (SiO$_2$, cyclohexane/EtOAc 13/1) to give 3β,17β-di(dimethyltert-butylsilyloxy)-7-oxa-7a-homoandrostane-6-one and 3α,17β-di(dimethyltert-butylsilyloxy)-7-oxa-7a-homoandrostane-6-one (90/10 mixture, 101 mg, 14%). $^1$H-NMR (300 MHz, acetone-d$_6$, ppm from TMS): δ 4.21-4.09 (m, 1H), 3.93 (m, 1H), 3.69-3.57 (m, 1H), 3.64 (m, 1H), 3.10 (m, 1H), 2.02-1.02 (m, 17H), 0.89 (s, 9H), 0.88 (s, 9H), 0.86 (s, 3H), 0.77 (s, 3H), 0.06 (s, 6H), 0.04 (s, 3H), 0.03 (s, 3H) and 3β,17β-di(dimethyltert-butylsilyloxy)-6-oxa-7a-homoandrostane-7-one and 3α,17β-di(dimethyltert-butylsilyloxy)-6-oxa-7a-homoandrostane-7-one (90/10 mixture, 203 mg, 28%) $^1$H-NMR (300 MHz, acetone-d$_6$, ppm from TMS): δ 4.48 (m, 1H), 3.72-3.60 (m, 1H), 3.65 (m, 1H), 2.64-2.53 (m, 1H), 2.34-2.25 (m, 1H), 2.602-1.00 (m, 17H), 0.90 (s, 3H), 0.89 (s, 9H), 0.88 (s, 9H), 0.76 (s, 3H), 0.07 (s, 6H), 0.04 (s, 3H), 0.03 (s, 3H).

To a stirred solution of 3β,17β-di(dimethyltert-butylsilyloxy)-7-oxa-7a-homoandrostane-6-one and 3α,17β-di(dimethyltert-butylsilyloxy)-7-oxa-7a-homoandrostane-6-one (90/10 mixture, 680 mg) in THF (15 mL) 1 M solution TBAF in THF (7.40 mL) was added. After 48 h the mixture was quenched with 5% Na$_2$HPO$_4$ aqueous solution and extracted with CH$_2$Cl$_2$. The combined organic extracts were washed with H$_2$O, dried over Na$_2$SO$_4$ and evaporated to dryness. The residue was purified by flash chromatography (SiO$_2$, CH$_2$Cl$_2$/acetone 80/20) to give 3β,17β-dihydroxy-7-oxa-7a-homoandrostane-6-one and 3α,17β-dihydroxy-7-oxa-7a-homoandrostane-6-one (90/10 mixture, 390 mg, 98%). $^1$H-NMR (300 MHz, DMSO-d$_6$, ppm from TMS): δ 4.56 (bb, 1H), 4.52 (bb, 1H), 4.14 (m, 1H), 3.83 (bb, 1H), 3.46-3.36 (m, 1H), 3.31 (m, 1H), 3.03 (m, 1H), 1.93-0.87 (m, 17H), 0.74 (s, 3H), 0.63 (s, 3H).

7-Oxa-7a-homoandrostane-3,6,17-trione was prepared in 84% yield from 3β,17β-dihydroxy-7-oxa-7a-homoandrostane-6-one and 3α,17β-dihydroxy-7-oxa-7a-homoandrostane-6-one (90/10 mixture, 390 mg) by the procedure described above for the preparation of 3β,17β-di(dimethyltert-butylsilyloxy)-androstane-6-one and 3α,17β-di(dimethyltert-butylsilyloxy)-androstane-6-one (90/10 mixture, Prepn. 12). The crude product was purified by flash chromatography (SiO$_2$, hexane/acetone 80/20) to give 7-oxa-7a-homoandrostane-3,6,17-trione (II-m, 330 mg). $^1$H-NMR (300 MHz, DMSO-d$_6$, ppm from TMS): δ 4.31 (bb, 1H), 4.05 (bb, 1H), 3.60 (m, 1H), 2.84 (bb, 1H), 2.47-1.10 (m, 16H), 0.94 (s, 3H), 0.82 (s, 3H).

3β,17β-Dihydroxy-6-oxa-7a-homoandrostane-7-one and 3α,17β-dihydroxy-6-oxa-7a-homoandrostane-7-one (90/10 mixture) was prepared in 96% yield from 3β,17β-di(dimethyltert-butylsilyloxy)-6-oxa-7a-homoandrostane-7-one and 3β,17β-di(dimethyltert-butylsilyloxy)-6-oxa-7a-homoandrostane-7-one (90/10 mixture, 1.32 g) by the procedure described above for the preparation 3β,17β-dihydroxy-7-oxa-7a-homoandrostane-6-one and 3β,17β-dihydroxy-7-oxa-7a-homoandrostane-6-one (90/10 mixture, Prepn. 12). The crude product was purified by flash chromatography (SiO$_2$, hexane/acetone 60/40) to give 3β,17β-dihydroxy-6-oxa-7a-homoandrostane-7-one and 3β,17β-dihydroxy-6-oxa-7a-homoandrostane-7-one (90/10 mixture, 740 mg). $^1$H-NMR (300 MHz, DMSO-d$_6$, ppm from TMS): δ 4.72 (bb, 1H), 4.51 (bb, 1H), 4.43 (m, 1H), 3.46-3.36 (m, 1H), 3.32 (m, 1H), 2.16 (m, 1H), 2.13 (m, 1H), 1.96-0.81 (m, 17H), 0.76 (s, 3H), 0.62 (s, 3H).

6-Oxa-7a-homoandrostane-3,7,17-trione was prepared in 70% yield from 3β,17β-dihydroxy-6-oxa-7a-homoandrostane-7-one and 3β,17β-dihydroxy-6-oxa-7a-homoandrostane-7-one (90/10 mixture, 620 mg) by the procedure described above for the preparation of 3β,17β-di(dimethyltert-butylsililoxy)androstane-6-one and 3α,17β-di(dimethyltert-butylsililoxy)androstane-6-one (90/10 mixture, Prepn. 12). The crude product was purified by flash chromatography (SiO$_2$, hexane/acetone/CH$_2$Cl$_2$ 50/25/25) to give the title compound II-n (440 mg). $^1$H-NMR (300 MHz, acetone-d$_6$, ppm from TMS): δ 4.81 (m, 1H), 2.87-2.67 (m, 2H), 2.57-2.40 (m, 4H), 2.33-2.22 (m, 1H), 2.17-1.21 (m, 12H), 01.15 (s, 3H), 0.92 (s, 3H).

Preparation 13

7a-Oxa-7a-homoandrostane-3,7,17-trione (II-o)

3β,17β-Dihydroxyandrostan-7-one was prepared in 96% yield from 3β,17β-dihydroxyandrost-5-en-7-one (700 mg) by the procedure described above for the preparation of 3,3:17,17-bis(ethylendioxy)androstane-7-one (Prepn. 9). The crude product was purified by flash chromatography (SiO$_2$, hexane/acetone/CH$_2$Cl$_2$ 10/10/10) to give 3β,17β-dihydroxyandrostane-7-one (670 mg). $^1$H-NMR (300 MHz, DMSO-d$_6$, ppm from TMS): δ 4.53 (bb, 1H), 4.44 (bb, 1H), 3.47-3.27 (m, 2H), 2.45-2.31 (m, 2H), 2.05-1.91 (m, 1H), 1.89-0.78 (m, 17H), 0.99 (s, 3H), 0.59 (s, 3H).

3β,17β-Dihydroxy-7a-oxa-7a-homoandrostane-7-one was prepared in 86% yield from 3β,17β-dihydroxyandrostan-7-one (730 mg) by the procedure described above for the preparation of 3β,17β-di(dimethyltert-butylsililoxy)-7-oxa-7a-homoandrostane-6-one and 3α,17β-di(dimethyltert-butylsililoxy)-7-oxa-7a-homoandrostane-6-one (90/10 mixture, Prepn. 12). The crude product was purified by flash chromatography (SiO$_2$, hexane/acetone/CH$_2$Cl$_2$ 40/30/30) to give 3β,17β-dihydroxy-7a-oxa-7a-homoandrostane-7-one (660 mg). $^1$H-NMR (300 MHz, DMSO-d$_6$, ppm from TMS): δ 4.55 (bb, 2H), 4.40 (bb, 1H), 3.54-3.43 (m, 1H), 3.32 (m, 1H), 2.99 (m, 1H), 1.93-0.94 (m, 18H), 0.91 (s, 3H), 0.61 (s, 3H).

7a-Oxa-7a-homoandrostane-3,7,17-trione was prepared in 81% yield from 3β,17β-dihydroxy-7a-oxa-7a-homoandrostane-7-one (300 mg) by the procedure described above for the preparation of 3β,17β-di(dimethyltert-butylsililoxy)androstane-6-one and 3α,17β-di(dimethyltert-butylsililoxy)androstane-6-one (90/10 mixture, Prepn. 12). The crude product was purified by flash chromatography (SiO$_2$, hexane/acetone/CH$_2$Cl$_2$ 50/25/25) to give the title compound II-o (240 mg). $^1$H-NMR (300 MHz, DMSO-d$_6$, ppm from TMS): δ 4.73 (m, 1H), 3.16 (m, 1H), 2.47-2.27 (m, 3H), 2.13 (m, 1H), 2.08-1.33 (m, 13H), 1.22 (m, 1H), 1.16 (s, 3H), 0.80 (s, 3H).

Preparation 14

6-Oxa-5β-androstane-3,7,17-trione (II-p)

To a stirred solution of 3β-hydroxyandrost-5-en-7,17-dione in t-BuOH (385 mL) and 0.25 M K$_2$CO$_3$ aqueous solution (97.5 mL) under vigorous stirring at 60° C., 0.37 M NaIO$_4$ aqueous solution (63.4 mL) and 0.05 M KMnO$_4$ aqueous solution (7.3 mL) was added. After 15 minutes, 0.05 M KMnO$_4$ aqueous solution (5 mL) was added and then 0.37 M NaIO$_4$ aqueous solution (253.6 mL) was added dropwise over 0.5 h. After 5 minutes 0.05 M KMnO$_4$ aqueous solution (3 mL) was added. After 1.5 h at 60° C. the suspension was cooled with an ice-bath and then quenched by careful addition of a 10% aqueous solution of NaHSO$_3$. To the concentrated aqueous solution NaCl (100 g) was added and then extracted with CH$_2$Cl$_2$. The combined organic extracts were washed with H$_2$O, dried over Na$_2$SO$_4$ and evaporated to dryness to give 3β-hydroxy-5,17-dioxo-5,7-seco-B-norandrost-7-oic acid (4.16 g, 78%). $^1$H-NMR (300 MHz, DMSO-d$_6$, ppm from TMS): δ12.17 (bb, 1H), 4.65 (bb, 1H), 4.17 (bb, 1H), 3.05 (bb, 1H), 2.44-2.13 (m, 3H), 2.13-1.18 (m, 10H), 0.90 (s, 3H), 0.76 (s, 3H).

To a stirred solution of 3β-hydroxy-5,17-dioxo-5,7-seco-B-norandrost-7-oic acid (200 mg) in toluene (2.9 mL) and MeOH (4 mL), 2 M (trimethylsilyl)diazomethane solution in hexanes (0.412 mL) at 0° C. was added dropwise. After 2 h SiO$_2$ was added and the mixture was purified by flash chromatography (SiO$_2$, CH$_2$Cl$_2$/MeOH 90/10) to give methyl 3β-hydroxy-5,17-dioxo-5,7-seco-B-norandrost-7-oate (180 mg, 88%). $^1$H-NMR (300 MHz, DMSO-d$_6$, ppm from TMS): δ 4.66 (bb, 1H), 4.19 (bb, 1H), 3.43 (s, 3H), 2.98 (m, 1H), 2.43-2.24 (m, 3H), 2.11-1.95 (m, 2H), 1.91-1.19 (m, 11H), 0.87 (s, 3H), 0.77 (s, 3H).

To a stirred solution of methyl 3β-hydroxy-5,17-dioxo-5,7-seco-B-norandrost-7-oate (900 mg) in THF (9 mL), at 0° C. under N$_2$, NaBH$_4$ (306 mg) was added in portions over 15 min. After stirring for 1.5 h at room temperature, the mixture was quenched by careful addition of 1N HCl to acid pH and extracted with CH$_2$Cl$_2$/tBuOH 9/1. The combined organic extracts were dried over Na$_2$SO$_4$ and evaporated to dryness to give 3β,17β-dihydroxy-6-oxa-5β-androstan-7-one (800 g, 94%). $^1$H-NMR (300 MHz, DMSO-d$_6$, ppm from TMS): δ 4.61 (bb, 1H), 4.49 (bb, 1H), 4.24 (bb, 1H), 3.57 (bb, 1H), 3.45 (m, 1H), 2.42 (m, 1H), 2.08-1.11 (m, 14H), 1.04 (m, 1H), 0.97-0.85 (m, 1H), 0.93 (s, 3H), 0.64 (s, 3H).

To a stirred solution of NaBrO$_3$ (664 mg) in H$_2$O (9 mL) RuO$_2$ dihydrate (24 mg) and EtOAc (18 mL) were added. After 10 minutes 3β,17β-dihydroxy-6-oxa-5β-androstan-7-one (450 mg) was added. After stirring for 15 minutes at room temperature, the mixture was quenched by careful addition of i-PrOH and extracted with EtOAc. The combined organic extracts were dried over Na$_2$SO$_4$ and evaporated to dryness. The crude product was triturated with hexane/Et$_2$O 1/1 and the precipitate was filtered to give the title compound II-p (360 mg, 80%). $^1$H-NMR (300 MHz, acetone-d$_6$, ppm from TMS): δ 4.61 (bb, 1H), 2.98-2.87 (m, 1H), 2.83-2.73 (m, 2H), 2.64-2.18 (m, 5H), 1.94-1.46 (m, 8H), 1.32-1.18 (m, 1H), 1.25 (s, 3H), 0.92 (s, 3H).

Preparation 15

2-N-Methylaminoethoxyamine dihydrochloride (III-a)

To a suspension of potassium hydroxide (19.7 g) in DMSO (200 mL), under vigorous stirring, benzophenone oxime (20.2 g) was added. A solution of N-methyl-2-chloroethylamine hydrochloride (5.2 g) in DMSO (40 mL) was added dropwise. After 2.5 hrs at room temperature the reaction was poured into ice/water (400 mL), acidified with 37% HCl to pH 2.5 and washed with $Et_2O$. The aqueous layer was treated with powdered KOH to pH 10 and extracted three times with $Et_2O$; the combined organic layers were washed with water, brine, dried over $Na_2SO_4$ and the solvent evaporated to dryness. Purification by flash chromatography ($SiO_2$, $CHCl_3$:MeOH:AcOH from 9:1:0.1 to 7:3:0.3) gave benzophenone O-(2-N-methylaminoethyl)oxime (4.65 g, 62%) as a viscous oil. $^1$H-NMR (300 MHz, DMSO-$d_6$, ppm from TMS): δ 7.51-7.25 (10H, m), 4.13 (2H, t), 2.72 (2H, t), 2.26 (3H, s), 1.60 (1H, bb).

Benzophenone O-(2-N-methylaminoethyl)oxime (4.65 g) was suspended in 6N HCl (24 mL) and the mixture refluxed for 2 hrs. The reaction was cooled and extracted with $Et_2O$. The aqueous layer was evaporated to dryness to give the title compound III-a (1.78 g, 80%) as a hygroscopic white solid. $^1$H-NMR (300 MHz, DMSO-$d_6$, ppm from TMS): δ 10.5 (5H, bb), 4.26 (2H, t), 3.22 (2H, t), 2.55 (3H, s).

Preparation 16

3-N-Methylaminopropoxyamine dihydrochloride (III-b)

Benzophenone O-(3-N-methylaminopropyl)oxime was prepared in 62% yield from benzophenone oxime and N-methyl-3-chloropropylamine hydrochloride by the procedure described above for the preparation of benzophenone O-(2-N-methylaminoethyl)oxime (Prep. 15). $^1$H-NMR (300 MHz, DMSO-$d_6$, ppm from TMS): δ 9.20 (2H, bb), 7.37 (10H, m), 4.14 (2H, t), 2.70 (2H, t), 2.36 (3H, s), 1.87 (2H, m), 1.83 (3H, s).

The title compound III-b was prepared in 80% yield from benzophenone O-(3-N-methylaminopropyl)oxime by the procedure described above for the preparation 2-N-methylaminoethoxyamine dihydrochloride (III-a, Prep. 15). $^1$H-NMR (300 MHz, DMSO-$d_6$, ppm from TMS): δ 11.08 (3H, bb), 9.10 (2H, bb), 4.10 (2H, t), 2.91 (2H, m), 2.50 (3H, s), 1.96 (2H, m).

Preparation 17

3(R)-Pyrrolidinyloxyamine dihydrochloride (III-c)

To a solution of N-tert-butoxycarbonyl-(S)-pyrrolidinol (10.0 g) and triethylamine (8.2 mL) in $CH_2Cl_2$ (150 mL) at 0° C., methanesulfonyl chloride (4.34 mL) was added. After stirring at room temperature for 3 h, the reaction mixture was poured into ice/water and extracted with $CH_2Cl_2$. The organic phase was washed with 5% aqueous $NaHCO_3$, water, brine, dried and evaporated to dryness to give an oil which solidified after standing overnight in the refrigerator. The solid was triturated with $Et_2O$ to give N-tert-butoxycarbonyl-(S)-3-pyrrolidinyl methansulfonate (13.0 g, 92%) as a light yellow solid. $^1$H-NMR (300 MHz, DMSO-$d_6$, ppm from TMS): δ 5.23 (1H, m), 3.60-3.10 (4H, m), 3.23 (3H, s), 2.11 (2H, m), 1.39 (9H, s).

To a suspension of KOH powder (4.86 g) in DMSO (250 mL) under vigorous stirring, benzophenone oxime (7.86 g) was added. After stirring at room temperature for 30 min, a solution of N-tert-butoxycarbonyl-(S)-3-pyrrolidinyl methansulfonate (10 g) in DMSO (70 mL) was added. After 18 h at room temperature the reaction was poured into iced water (900 mL) and extracted with $Et_2O$. The combined organic layers were washed with water, brine, dried and the solvent evaporated. Benzophenone 0-[(R)-3-pyrrolidinyl]oxime was obtained (13.0 g, 96%) as a white solid and used without purification in the next step. $^1$H-NMR (300 MHz, DMSO-$d_6$, ppm from TMS): δ 7.50-7.20 (10H, m), 4.84 (1H, m), 3.50-3.00 (4H, m), 2.01 (2H, m), 1.38 (9H, s).

Benzophenone 0-[(R)-3-pyrrolidinyl]oxime (13.0 g) was suspended in 6N HCl (250 mL) and the mixture was refluxed for 2 h. After cooling, the reaction was extracted with $Et_2O$. The aqueous layer was evaporated to give a crude brown solid which was treated with 0.34 g of activated carbon in absolute EtOH (255 mL) at reflux for 2 h. The solid obtained after evaporation was crystallized with 96% EtOH (40 mL) to give the title compound III-c (2.98 g, 72%), as an off white solid. $^1$H-NMR (300 MHz, DMSO-$d_6$, ppm from TMS): δ 11.22 (3H, bb), 9.74 (1H, bb), 9.54 (1H, bb), 4.98 (1H, m), 3.60-3.00 (4H, m), 2.40-2.00 (2H, m).

Preparation 18

3(E)-[2-(9H-Fluoren-9-ylmethylcarbonyl)aminoethoxyimino)-6-aza-7a-homo-androstane-7,17-dione (II-q) and 3(Z)-[2-(9H-fluoren-9-ylmethylcarbonyl)-aminoethoxyimino)-6-aza-7a-homoandrostane-7,17-dione (II-r)

A mixture of the title compounds was prepared from (E,Z) 3-(2-aminoethoxyimino)-6-aza-7a-homoandrostane-7,17-dione hydrochloride (I-aa, Example 1, 1.24 g) by the procedure described above for the preparation of 3(E)-[2-(9H-fluoren-9-ylmethylcarbonyl)aminoethoxyimino)-6-aza-6-methyl-7a-homo-androstane-7,17-dione (II-c) and 3(Z)-[2-(9H-fluoren-9-ylmethylcarbonyl)-aminoethoxyimino)-6-aza-6-methyl-7a-homoandrostane-7,17-dione (II-d, Prepn. 3). The crude product was purified by flash chromatography ($SiO_2$, cyclohexane/iPrOH/$CH_2Cl_2$ 50/5/45) to give 3(Z)-[2-(9H-fluoren-9-ylmethylcarbonyl)aminoethoxyimino)-6-aza-7a-homo-androstane-7,17-dione (II-r, 820 mg, 46%). and 3(E)-[2-(9H-fluoren-9-ylmethylcarbonyl)aminoethoxyimino)-6-aza-7a-homo-androstane-7,17-dione (II-q, 830 mg, 47%). II-r: $^1$H-NMR (300 MHz, DMSO-$d_6$, ppm from TMS): δ 7.88 (m, 2H), 7.77 (m, 2H), 7.40 (m, 2H), 7.37 (bb, 1H), 7.31 (m, 2H), 7.17 (bb, 2H), 4.10 (m, 3H), 3.93 (t, 2H), 3.35 (m, 1H), 3.22 (m, 2H), 3.06 (m, 1H), 2.50-0.70 (m, 18H), 0.78 (s, 3H), 0.76 (s, 3H). II-q: $^1$H-NMR (300 MHz, DMSO-$d_6$, ppm from TMS): δ 7.88 (m, 2H), 7.67 (m, 2H), 7.40 (m, 2H), 7.34 (bb, 1H), 7.31 (m, 2H), 7.17 (bb, 1H), 4.25 (m, 3H), 3.93 (t, 2H), 3.39 (m, 1H), 3.21 (m, 3H), 2.85 (m, 1H), 2.50-0.80 (m, 18H), 0.79 (s, 3H), 0.75 (s, 3H).

Preparation 19

6-Oxa-7a-homoandrostane-3,17-dione (II-s)

To a stirred suspension of $LiAlH_4$ (165 mg) in THF under $N_2$ at 0° C. (14 mL) a solution of 3β,17β-di(dimethyltert-butylsilyloxy)-6-oxa-7a-homo-androstane-7-one (Prepn. 12, 240 mg) and $BF_3.Et_2O$ (1.96 mL) in THF (14 mL) was added dropwise and after 45 minutes the mixture was refluxed for 1 h. The suspension was cooled with an ice bath and then quenched by careful addition of a solution of THF/$H_2O$ 1/1 and then 2N HCl. The mixture was extracted with $Et_2O$ (3×) and then with $CH_2Cl_2$. The combined organic extracts were washed with 5% aqueous $NaHCO_3$, dried over $Na_2SO_4$, filtered and evaporated to dryness. The residue was purified by flash chromatography ($SiO_2$, cyclohexane/$CH_2Cl_2$/acetone 1/1/1) to give 6-oxa-7a-homoandrostane-3β,17β-diol (50 mg, 25%). $^1$H-NMR (300 MHz, DMSO-$d_6$, ppm from TMS): δ 4.51 (d, 1H), 4.30 (d, 1H), 3.70-3.20 (m, 5H), 1.87-0.60 (m, 19H), 0.76 (s, 3H), 0.62 (s, 3H).

6-Oxa-7a-homoandrostane-3,17-dione was prepared from 6-oxa-7a-homoandrostane-3,17-diol by the procedure described above for the preparation of 3β,17β-di(dimethyl-tert-butylsililoxy)androstane-6-one and 3α,17β-di(dimethyl-tert-butylsililoxy)androstane-6-one (Prepn. 12). The mixture was stirred for 2 h and then SiO$_2$ was added. The mixture was purified by flash chromatography (SiO$_2$, cyclohexane/acetone 85/15) to give 6-oxa-7a-homoandrostane-3,17-dione (35%). $^1$H-NMR (300 MHz, acetone-d$_6$, ppm from TMS): δ 3.90-3.50 (m, 3H), 2.06-0.90 (m, 19H), 1.11 (s, 3H), 0.88 (s, 3H).

Preparation 20

7a-oxa-7a-homoandrostane-3,17-dione (II-t)

7a-Oxa-7a-homoandrostane-3β,17β-diol was prepared from 7a-oxa-7a-homoandrostane-3,7,17-trione (Prepn. 13) by the procedure described above for the preparation of 6-oxa-7a-homoandrostane-3β,17β-diol (Prepn. 19). The mixture was stirred for 2 h and then SiO$_2$ was added. The mixture was purified by flash chromatography (SiO$_2$, cyclohexane/acetone/CH$_2$Cl$_2$ 1/1/1) to give 7a-oxa-7a-homoandrostane-3,17-diol (65%). $^1$H-NMR (300 MHz, DMSO-d$_6$, ppm from TMS): δ 4.45 (d, 1H), 4.41 (d, 1H), 3.57-3.01 (m, 5H), 1.90-0.75 (m, 19H), 0.79 (s, 3H), 0.60 (s, 3H).

7a-Oxa-7a-homoandrostane-3,17-dione was prepared from 7a-oxa-7a-homoandrostane-3,17-diol by the procedure described above for the preparation of 6-oxa-7a-homoandrostane-3,17-dione (Prepn. 19). The mixture was stirred for 2 h and then SiO$_2$ was added. The mixture was purified by flash chromatography (SiO$_2$, cyclohexane/acetone/CH$_2$Cl$_2$ 70/15/15) to give the title compound II-t (85%). $^1$H-NMR (300 MHz, acetone-d$_6$, ppm from TMS): δ 3.75-3.50 (m, 3H), 2.15-1.15 (m, 19H), 1.18 (s, 3H), 0.87 (s, 3H).

Preparation 21

6-Azaandrostane-3,7,17-trione (II-u)

3β-Hydroxy-6-azaandrostane-7,17-dione was prepared from 3β-(t-butyldimethylsilyloxy)-6-azaandrostane-7,17-dione (*Heterocycles*, 38 (1994) 5, 1053-1060) by the procedure described above for the preparation of 3β,17β-dihydroxy-7-oxa-7a-homoandrostane-6-one and 3α,17β-dihydroxy-7-oxa-7a-homoandrostane-6-one (Prepn. 12). The mixture was stirred for 2 h and then SiO$_2$ was added. The mixture was purified by flash chromatography (SiO$_2$, EtOAc/EtOH/CH$_2$Cl$_2$ 50/10/40) to give 3β-hydroxy-6-azaandrostane-7,17-dione (83%). $^1$H-NMR (300 MHz, DMSO-d$_6$, ppm from TMS): δ 7.25 (s, 1H), 446 (d, 1H), 3.39 (m, 1H), 2.91 (dd, 1H), 2.40-0.90 (m, 17H), 0.80 (s, 3H), 0.78 (s, 3H).

6-Azaandrostane-3,7,17-trione was prepared from 3β-hydroxy-6-azaandrostane-7,17-dione by the procedure described above for the preparation of 3β,17β-di(dimethyl-tert-butylsilyloxy)androstane-6-one and 3α,17β-di(dimethyltert-butylsilyloxy)androstane-6-one (Prepn. 12). The mixture was stirred for 35 minutes, then SiO$_2$ was added and evaporated to dryness. The mixture was purified by flash chromatography (SiO$_2$, acetone/toluene 1/1) to give 6-azaandrostane-3,7,17-trione (75%). $^1$H-NMR (300 MHz, DMSO-d$_6$, ppm from TMS): δ 7.34 (s, 1H), 3.31 (dd, 1H), 2.57-1.07 (m, 17H), 0.99 (s, 3H), 0.83 (s, 3H).

Biological Studies and Results

The compounds of the present invention show affinity and inhibit the enzymatic activity of the Na$^+$,K$^+$-ATPase. To test the inhibition of the activity, the Na$^+$,K$^+$-ATPase was purified according to Jorghensen (Jorghensen P., BBA, 1974, 356, 36) and Erdmann (Erdmann E. et al., Arzneim. Forsh., 1984, 34, 1314) and the inhibition was measured as % of hydrolysis of $^{32}$P-ATP in the presence and absence of the tested compounds (Mall F. et al., Biochem. Pharmacol., 1984, 33, 47; see Table 1). As reference compound 22b ((EZ) 3-(2-aminoethoxy-imino)androstane-6,17-dione hydrochloride) is reported, already described by S. De Munari et al. in *J. Med. Chem.* 2003, 46(17), 3644-3654.

TABLE 1

Dog Kidney Na$^+$,K$^+$-ATPase Inhibition

| Example n° | Na$^+$,K$^+$-ATPase Inhibition IC$_{50}$, μM | Example n° | Na$^+$,K$^+$-ATPase Inhibition IC$_{50}$, μM |
|---|---|---|---|
| I-aa | 25 | I-ac | 19 |
| I-ad | 0.95 | I-aj | 6.5 |
| I-ak | 29 | I-am | 9.5 |
| I-an | 23 | I-ap | 35 |
| I-aq | 18 | I-ar | 7.5 |
| I-as | 5.9 | I-at | 48 |
| I-au | 68 | I-av | 27 |
| I-aw | 9.9 | I-ax | 4.8 |
| I-ay | 0.40 | I-az | 1.8 |
| I-ba | 0.14 | I-bd | 57 |
| I-be | 1.6 | I-bf | 1.9 |
| I-bg | 0.81 | I-bh | 0.24 |
| I-bi | 0.85 | I-bj | 2.2 |
| I-bk | 0.36 | I-bl | 2.5 |
| I-bm | 25 | I-bn | 61 |
| I-bo | 0.071 | I-bp | 0.040 |
| I-bq | 3.7 | I-br | 1.3 |
| I-bs | 0.13 | I-bt | 0.16 |
| I-bu | 1.1 | I-bv | 1.4 |
| Compd. 22b | 0.33 | | |

The ability of these compounds to lower blood pressure was tested by using animal models with genetic arterial hypertension, in particular, spontaneous hypertensive rats of the Milan (MHS) (Bianchi G., Ferrari P., Barber B. The Milan Hypertensive strain. In Handbook of hypertension. Vol. 4: Experimental and genetic models of hypertension. Ed. W. de jong-Elsevier Science Publishers B.V., 1984:328-349) and rats made hypertensive by chronic infusion of ouabain, according to Ferrari P., et al. *J. Pharm. Exp. Ther.* 1998, 285, 83-94.

The procedure adopted to test the antihypertensive activity of the compounds on the above mentioned model was the following: systolic blood pressure (SBP) and heart rate (HR) were measured by an indirect tail-cuff method.

To test the compounds in the MHS model one-month old hypertensive rats (MHS) were subdivided in two groups of at least 7 animals each, one receiving the compound and the other, the control group, receiving only the vehicle. The compound, suspended in Methocel 0.5% (w/v), was administered daily by mouth, for five weeks. SBP and HR were measured weekly 6 hours after the treatment.

The compounds of the present invention possess a higher potency and efficacy compared to compound 22b ((EZ) 3-(2-aminoethoxyimino)androstane-6,17-dione hydrochloride) reported by S. De Munari et al. in *J. Med. Chem.* 2003, 46(17), 3644-3654. The activity of the reference compound 22b and some new compounds in lowering blood pressure in spontaneous hypertensive MHS rats is shown in the following table and is expressed as the decrease in systolic blood pressure (expressed both as decrease in mmHg and percentage) and the variation of heart rate (beats per minute) at the end of the five week treatment period, versus the control group which received only the vehicle.

Systolic Blood Pressure Fall in Spontaneous Hypertensive Rats (MHS)

| EXAMPLE n° | RATS | DOSE* μg/kg/os | SBP - mm Hg | SBP - % | HR beats/ min. | HR % |
|---|---|---|---|---|---|---|
| Comp. I-aa | 8 | 10 | 12.3 +/- 1.1 | 7.1 | -7.5 | -2.1 |
| Comp. I-aa | 8 | 1 | 10.0 +/- 2.1 | 6.0 | -12.4 | -3.6 |
| Comp. I-aa | 8 | 0.1 | 11.3 +/- 1.5 | 6.5 | -16.3 | -4.8 |
| Comp. I-aa | 8 | 0.01 | 8.8 +/- 1.6 | 5.2 | -7.5 | -4.8 |
| Comp. I-aa | 8 | 0.001 | 1.0 +/- 1.1 | 0.0 | -17.5 | -5.0 |
| Comp. I-ac | 8 | 10 | 7.2 +/- 0.7 | 4.2 | 0.0 | 0.0 |

-continued

| EXAMPLE n° | RATS | DOSE* μg/kg/os | SBP - mm Hg | SBP - % | HR beats/ min. | HR % |
|---|---|---|---|---|---|---|
| Comp. 22b | 7 | 100 | 10.7 +/- 7.5 | 6.6 | -7.2 | -2.0 |
| Comp. 22b | 7 | 10 | 3.6 +/- 4.8 | 2.2 | -15.8 | -4.3 |

*in Methocel 0.5% w/v

As further demonstration of the blood pressure lowering effect in hypertensive ouabain-sensitive rats, the compound, suspended in Methocel 0.5% (w/v), was administered daily at the dose of 10 μg/kg/day by mouth for four weeks. SBP and HR were measured weekly 6 hours after the treatment.

Systolic Blood Pressure Fall in Hypertensive Ouabain-Sensitive Rats (OS Rats)

| EXAMPLE n° | RATS | SBP mm Hg | SBP - mm Hg | SBP - % | HR beats/min. |
|---|---|---|---|---|---|
| Comp. I-aa | 8 | 153.0 | 17.0 | 10.0 | 385 |
| Comp. I-ap | 8 | 154.0 | 15.0 | 9.4 | 387 |
| OS rats | 8 | 170.0 | — | — | 368 |
| Control | 8 | 150.0 | — | — | 376 |

Moreover the compounds of the present invention possess positive inotropic features, as shown by slow intravenous infusion in anesthetized guinea pig according to Cerri et al. (Cerri A. et al., J. Med. Chem. 2000, 43, 2332) and have a low toxicity when compared with standard cardiotonic steroids, e.g. digoxin. The compounds of the present invention possess a higher potency and/or a better therapeutic ratio and/or a longer duration of action compared to compound 22b ((EZ) 3-(2-aminoethoxyimino)androstane-6,17-dione hydrochloride) reported by S. De Munari et al. in J. Med. Chem. 2003, 46(17), 3644-3654.

The activity of compounds I-ba and I-bk on the above mentioned tests is shown in the following Table 2. The inotropic effect is shown as maximum increase in contractile force ($E_{max}$ measured as +dP/dT$_{max}$), dose inducing maximum positive inotropic effect ($ED_{max}$), inotropic potency ($ED_{80}$, dose increasing +dP/dT$_{max}$ by 80%); the toxicity as the ratio between lethal dose and inotropic potency (calculated in the died animals); the maximum dose infused in the survived animals; the duration of the inotropic effect as the decrease of the effect from the $ED_{max}$ measured 20 minutes after the end of the infusion.

TABLE 2

Inotropic Effect and Lethal Dose in Anesthetized Guinea-pig.

Slow intravenous infusion (over 90 minutes) in anesthetized guinea-pig

| Example n° | $E_{max}$ % increase in +dP/dT$_{max}$ | $ED_{max}$ μmol/kg | $ED_{80}$ μmol/kg | Dead/ treated | Lethal dose/ $ED_{80}$ | Maximum dose infused μmol/kg | % decrease from $E_{max}$ after 20 min from the end of the infusion |
|---|---|---|---|---|---|---|---|
| I-ba | 218 | 10.1 | 1.68 | 0/3 | nd | 50.0 | 55 |
| I-bk | 254 | 23.9 | 2.11 | 0/3 | nd | 25.3 | 50 |
| digoxin | 158 | 0.65 | 0.29 | 10/10 | 4.0 | 1.16 | 100 |
| compd 22b | 182 | 5.74 | 1.82 | 7/8 | 22.6 | 32.1 | 100 |

As reported in Table 2, compounds I-ba and I-bk show positive inotropic effects with higher safety ratios than those displayed by digitoxin and compd 22b. In fact the lethal dose/$ED_{80}$ ratio is not determinable, since no animals died. Further, I-ba and I-bk have prolonged action as shown by the persistence of the inotropic effect after stopping the infusion. Higher doses were not tested for I-ba and I-bk since their maximum increase in contractile force were higher than those displayed by digoxin and compd 22b.

The invention claimed is:
1. A compound of formula (I):

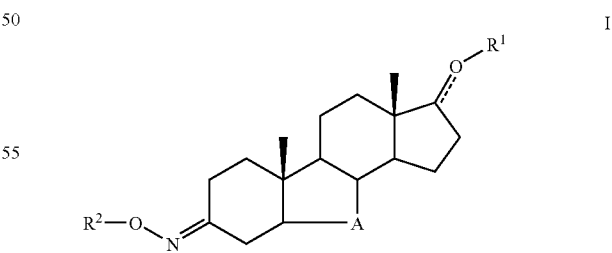

wherein:
A is a divalent group selected from the group consisting of

⁓CH$_2$CH$_2$CH$_2$⁓,  ⁓CH(OR$^3$)CH$_2$CH$_2$⁓,

⁓CH$_2$CH(OR$^3$)CH$_2$⁓,  ⁓C(=X)CH$_2$CH$_2$⁓,

-continued

∿∿CH₂C(=X)CH₂∿∿, ∿∿BCH₂CH₂∿∿,

∿∿CH₂BCH₂∿∿, ∿∿BCH₂∿∿, ∿∿BC(=X)CH₂∿∿,

∿∿C(=X)BCH₂∿∿, and ∿∿BC(=X)∿∿, wherein the ∿∿ symbols indicate α or β single bonds which connect the A group to the androstane skeleton at position 5 or 8;

B is oxygen or NR⁴, wherein R⁴ is H, C₁-C₆ alkyl group, or formyl when A is

∿∿BCH₂CH₂∿∿, ∿∿CH₂BCH₂∿∿, or ∿∿BCH₂∿∿;

$R^3$ is H or $C_1$-$C_6$ alkyl group;
X is oxygen, sulphur or $NOR^5$;
$R^5$ is H or $C_1$-$C_6$ alkyl group;
$R^1$ is H, $C_1$-$C_6$ alkyl group or $C_2$-$C_6$ acyl group when the bond ═ in position 17 of the androstane skeleton is a single bond; or
$R^1$ is not present when the bond ═ in position 17 is a double bond;
$R^2$ is $DNR^6R^7$ or the group

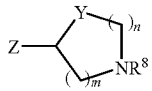

wherein D or Z is linked to the oxygen atom;
D is a $C_2$-$C_6$ linear or branched alkylene or a $C_3$-$C_6$ cycloalkylene, optionally containing a phenyl ring;
$R^6$ and $R^7$ are the same or different and are H, $C_1$-$C_6$ alkyl, phenyl-$C_1$-$C_4$ alkyl or $C(=NR^9)NHR^{10}$; or
$R^6$ and $R^7$, taken together with the nitrogen atom to which they are linked, form an unsubstituted or substituted saturated or unsaturated mono heterocyclic 4-, 5- or 6- membered ring, optionally containing another heteroatom selected from the group consisting of oxygen, sulphur and nitrogen; or
$R^6$ and $R^7$ are optionally substituted with one or more hydroxy, methoxy, or ethoxy groups; or
one of $R^6$ and $R^7$ is $C(=NR^9)NHR^{10}$ and the other is H;
$R^8$ is H, $C_1$-$C_6$ linear or branched alkyl, optionally substituted with one or more hydroxy, methoxy, ethoxy, or $C(=NR^9)NHR^{10}$;
$R^9$ and $R^{10}$ are the same or different and are H, $C_1$-$C_6$ linear or branched alkyl group; or
$R^9$ and $R^{10}$, taken together with the nitrogen atoms and the guanidinic carbon atom, form an unsubstituted or substituted saturated or unsaturated mono heterocyclic 5- or 6-membered ring optionally containing another heteroatom selected from the group consisting of oxygen, sulphur and nitrogen;
Z is a $C_1$-$C_4$ linear or branched alkylene or a single bond;
Y is $CH_2$, oxygen, sulphur or $NR^{11}$;
$R^{11}$ is H, or $C_1$-$C_6$, alkyl group;
n is 0, 1, 2 or 3;
m is 0, 1, 2 or 3;

the symbol ═ in position 17 is, independently, a single or double bond, and when it is a single exocyclic bond in position 17, it is an α or β single bond.

2. The compound according to claim 1, wherein A is selected from the group consisting of:

∿∿CH₂CH₂CH₂∿∿, ∿∿BCH₂CH₂∿∿,

∿∿BC(=X)CH₂∿∿ and ∿∿C(=X)BCH₂∿∿.

3. The compound according to claim 1, wherein $R_6$ and $R_7$ are the same or different, and are selected from the group consisting of H, and $C_1$-$C_6$ alkyls.

4. The compound according to claim 1 selected from the group consisting of:
(E, Z) 3-(2-Aminoethoxyimino)-6-aza-7a-homoandrostane-7,17-dione hydrochloride;
(E, Z) 3-(3-N-Methylaminopropoxyimino)-6-aza-7a-homoandrostane-7,17-dione fumarate;
(E, Z) 3[3-(R)-Pyrrolidinyl]oxyimino-6-aza-7a-homoandrostane-7,17-dione fumarate;
(E, Z) 3-(2-Aminoethoxyimino)-6-aza-7a-homo-7-thioxoandrostane-17-one hydrochloride;
(E, Z) 3-(2-Aminoethoxyimino)-6-aza-7a-homoandrostane-17-one dihydrochloride;
(E, Z) 3-[3-(R)-Pyrrolidinyl]oxyimino-6-aza-7a-homoandrostane-17-one dihydrochloride;
(E, Z) 3-(2-Aminoethoxyimino)-6-aza-6-formyl-7a-homoandrostane-17-one hydrochloride;
(E, Z) 3[3-(R)-Pyrrolidinyl]oxyimino-6-aza-6-formyl-7a-homoandrostane-1 7-one hydrochloride;
3-(E,Z)-(2-Aminoethoxyimino)-6-aza-7a-homo-7-(Z)-hydroxyiminoandrostane-17-one hydrochloride;
3-(E,Z)-(3-N-Methyl aminopropoxyimino)-6-aza-7a-homo-7-(Z)- hydroxyiminoandrostane-17-one hydrochloride;
3-(E,Z)-[3-(R)-Pyrrolidinyl]oxyimino-6-aza-7a-homo-7-(Z)- hydroxyiminoandrostane-17-one hydrochloride;
(E,Z) 3-(2-Aminoethoxyimino)-6-aza-7a-homo-7-(Z)-methoxyiminoandrostane-17-one hydrochloride;
3-(E,Z)-[3-(R)-Pyrrolidinyl]oxyimino-6-aza-7a-homo-7-(Z)- methoxyiminoandrostane-17-one hydrochloride;
(E, Z) 3-(2-Aminoethoxyimino)-7a-aza-7a-homoandrostane-7,17-dione hydrochloride;
(E, Z) 3-(3-N-Methylaminopropoxyimino)-7a-aza-7a-homoandrostane-7,17- dione hydrochloride;
(E, Z) 3-[3-(R)-Pyrrolidinyl]oxyimino-7a-aza-7a-homoandrostane-7,17-dione hydrochloride;
(E, Z) 3-(2-Aminoethoxyimino)-7a-aza-7a-homoandrostane-17-one difumarate;
(E, Z) 3 -(3-N-Methyl aminopropoxyimino)-7a-aza-7a-homoandrostane-1 7-one difumarate;
(E, Z) 3-[3-(R)-Pyrrolidinyl]oxyimino-7a-aza-7a-homoandrostane-17-one difumarate;
(E, Z) 3-[3 -(R)-Pyrrolidinyl]oxyimino-7a-aza-7a-formyl-7a-homoandrostane-1 7-one hydrochloride;
(E, Z) 3-(2-Aminoethoxyimino)-6-oxa-7a-homoandrostane-7,17-dione fumarate;
(E, Z) 3-(2-Aminoethoxyimino)-7-oxa-7a-homoandrostane-6,17-dione hydrochloride;
(E,Z)-3-(3-N-Methylaminopropoxyimino)-7-oxa-7a-homoandrostane-6,17-dione hydrochloride;
(E, Z) 3-[3-(R)-Pyrrolidinyl]oxyimino-7-oxa-7a-homoandrostane-6,1 7-dione hydrochloride;

(E, Z) 3-(2-Aminoethoxyimino)-7a-oxa-7a-homoandrostane-7,17-dione hydrochloride;
(E, Z) 3-(3-N-Methylaminopropoxyimino)-7a-oxa-7a-homoandrostane-7,17-dione hydrochloride;
(E, Z) 3-[3-(R)-Pyrrolidinyl]oxyimino-7a-oxa-7a-homoandrostane-7,17-dione hydrochloride;
(E, Z) 3-(2-Aminoethoxyimino)-6-oxa-5β-androstan-7,17-dione hydrochloride;
(E, Z) 3-(2-Aminoethoxyimino)-B-homoandrostane-17-one hydrochloride;
(E,Z)-3-[3-(R)-Pyrrolidinyl]oxyimino-B-homoandrostane-17-one hydrochloride;
(E,Z)-3-(3-N-Methylaminopropoxyimino)-6-oxa-7a-homoandrostane-7,17-dione fumarate;
(E, Z) 3-[3 -(R)-Pyrrolidinyl]oxyimino-6-oxa-7a-homoandrostane-7,17-dione fumarate;
(E,Z)-3-(2-Aminoethoxyimino)-6-oxa-7a-homoandrostane-17-one hydrochloride;
(E,Z)-3 -(2-Aminoethoxyimino)-7a-oxa-7a-homoandrostane-17-one hydrochloride;
(E, Z) 3-(2-Aminoethoxyimino)-6-azaandrostane-7,17-dione hydrochloride;
(E, Z) 3[3-(R)-Pyrrolidinyl]oxyimino-6-azaandrostane-7,17-dione fumarate;
(E) 3-(2-Aminoethoxyimino)-6-aza-7a-homo-androstane-7,17-dione fumarate; and
(Z) 3-(2-Aminoethoxyimino)-6-aza-7a-homo-androstane-7,17-dione fumarate.

5. A process for preparing the compound according to claim 1 comprising reacting a compound of general formula (II)

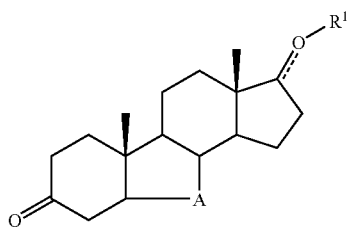

wherein the symbols A, $R^1$, and  are as defined in claim 1, with a compound of general formula (III)

$$R^2ONH_2 \qquad (III)$$

wherein $R^2$ is as defined in claim 1, the reaction being carried out in a polar solvent at a temperature ranging from 0° C. and the reflux temperature.

6. A pharmaceutical composition comprising a compound of claim 1 and excipients and/or pharmacologically acceptable diluents.

7. A pharmaceutical composition comprising one or more compounds according to claim 1 and excipients, stabilizers, pharmacologically acceptable diluents, or combinations thereof.

8. A process for the preparation of a pharmaceutical composition comprising mixing one or more compounds of claim 1 with suitable excipients, stabilizers, pharmaceutically acceptable diluents, or combinations thereof.

9. A method of treating a mammal suffering from a cardiovascular disorder, comprising administering a therapeutically effective amount of one or more compounds of claim 1 to the mammal in need thereof.

10. A method of treating a mammal suffering from a disease caused by the hypertensive effects of endogenous ouabain, comprising administering a therapeutically effective amount of one or more compounds of claim 1 to a mammal in need thereof.

11. The method according to claim 9, wherein the cardiovascular disorder is heart failure, hypertension or a combination thereof.

12. The method according to claim 10, wherein the disease caused by the hypertensive effects of endogenous ouabain is selected from the group consisting of renal failure progression in autosomal dominant polycystic renal disease (ADPKD), preeclamptic hypertension and proteinuria and renal failure progression in patients with adducin polymorphisms.

* * * * *